(12) United States Patent
Grossmann et al.

(10) Patent No.: US 8,877,895 B2
(45) Date of Patent: Nov. 4, 2014

(54) PROKARYOTIC EXPRESSION CONSTRUCT

(75) Inventors: Adelbert Grossmann, Eglfing (DE); Friederike Hesse, Munich (DE); Erhard Kopetzki, Penzberg (DE); Wilma Lau, Munich (DE); Christian Schantz, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 13/217,537

(22) Filed: Aug. 25, 2011

(65) Prior Publication Data

US 2012/0214200 A1  Aug. 23, 2012

(30) Foreign Application Priority Data

Aug. 30, 2010 (EP) .................................. 10008996
Oct. 15, 2010 (EP) .................................. 10187663

(51) Int. Cl.

| | |
|---|---|
| *C07K 19/00* | (2006.01) |
| *C07K 2/00* | (2006.01) |
| *C12N 15/70* | (2006.01) |
| *C12N 15/62* | (2006.01) |
| *C12P 21/02* | (2006.01) |
| *C12P 21/06* | (2006.01) |
| *C07K 14/775* | (2006.01) |

(52) U.S. Cl.
CPC ................ *C12N 15/62* (2013.01); *C12N 15/70* (2013.01); *C12P 21/02* (2013.01); *C07K 2319/21* (2013.01); *C07K 2319/02* (2013.01); *C07K 2319/70* (2013.01); *C12P 21/06* (2013.01); *C07K 2319/50* (2013.01); *C07K 14/775* (2013.01)
USPC .......................................... 530/350; 435/69.7

(58) Field of Classification Search
CPC ............. C07K 14/775; C07K 2319/02; C07K 2319/21; C07K 2319/50; C07K 2319/70; C12N 15/62; C12N 15/70; C12P 21/06; C12P 21/02
See application file for complete search history.

(56) References Cited

U.S. PATENT DOCUMENTS 6,897,039 B2 *  5/2005  Graversen et al. ........... 435/69.1

FOREIGN PATENT DOCUMENTS

| WO | 94/12631 A1 | 9/1994 | |
|---|---|---|---|
| WO | WO 2006/127757 A2 * | 11/2006 | ........... C07K 14/435 |
| WO | WO 2008/092019 A1 * | 7/2008 | ............. C07K 16/00 |

OTHER PUBLICATIONS

Kato et al, Molecular Cloning and Characterization of a cDNA for a Rice Sec31p Homolog, Biosci. Biotechnol. Biochem., 2000, 64, pp. 2490-2492.*
Database Genbank [Online] May 1, 2005, Heinemann et al.,: 'Facilities and methods for the high-throughput crystal structural analysis of human proteins' Database accession No. AAY18863, accessed Oct. 11, 2013.
Database PDB [Online] Seiradake et al.,: 'Chain C, Cav-2 Fibre Head In Complex With Car D1' Database accession No. 2J1K C, accessed Oct. 11, 2013.
Ryan et al., "Optimized bacterial expression of human apolipoprotein A-I" Protein Expr Purif. 27(1):98-103 ( 2003).

* cited by examiner

*Primary Examiner* — Julie Ha
*Assistant Examiner* — Li Ni Komatsu
(74) *Attorney, Agent, or Firm* — Robert C. Hall

(57) ABSTRACT

A pro-polypeptide which is useful for the expression of a polypeptide of interest in a prokaryotic cell. Therefore the pro-polypeptide is fused to the N-terminus of the polypeptide of interest. The pro-polypeptide as reported herein provides for improved expression yields and improves the handling of the fusion polypeptide (downstream processing, purification). For example, efficient endotoxin removal is effected while the protein of interest comprising the pro-polypeptide is bound e.g. to an affinity chromatography material. Thereafter the pro-polypeptide can efficiently be cleaved from the polypeptide of interest by the incorporated protease cleavage site with the cognate protease.

9 Claims, No Drawings

SEQUENCE LISTING

<160> NUMBER OF SEQ ID NOS: 85

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Ala Lys Arg Phe Lys Lys His
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala His Phe Trp Gln Gln Ala
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Asp Leu Pro Gln Thr His Ser Leu
1               5

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Glu Pro Asp
1

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Glu Pro Asp Ser Pro Gly Thr
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Met Cys Asp Leu Pro Gln Thr His Ser Leu
1               5                   10

<210> SEQ ID NO 7
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
                20                  25                  30

Ser Ala Val Gly Asn Ala Glu Ser Arg Tyr Val Leu Thr Gly Arg Tyr
            35                  40                  45

Asp Ser Ala Pro Ala Thr Asp Gly Ser Gly Thr Ala Leu Gly Trp Thr
50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 8
<211> LENGTH: 124
<212> TYPE: PRT
<213> ORGANISM: Artificial Sequence
<220> FEATURE:
<223> OTHER INFORMATION: Description of Artificial Sequence: Synthetic
      short amino acid sequence

<400> SEQUENCE: 8

Thr Asp Pro Glu Phe Gln Gln Gln Gln Leu Leu Asp Val Val Lys
1               5                   10                  15

Arg Gln Gln Glu Leu Leu Arg Leu Thr Val Trp Gly Thr Lys Asn Leu
                20                  25                  30

Gln Ala Arg Val Thr Ala Ile Glu Lys Tyr Leu Gln Asp Gln Ala Arg
            35                  40                  45

Leu Asn Ser Trp Gly Cys Ala Phe Arg Gln Val Cys His Thr Thr Val
50                  55                  60

Pro Trp Val Asn Asp Ser Leu Ala Pro Asp Trp Asp Asn Met Thr Trp
65                  70                  75                  80

Gln Glu Trp Glu Lys Gln Val Arg Tyr Leu Glu Ala Asn Ile Ser Lys
                85                  90                  95

Ser Leu Glu Gln Ala Gln Ile Gln Gln Glu Lys Asn Met Tyr Glu Leu
            100                 105                 110

Gln Lys Leu Asn Ser Trp Asp Ile Arg Ser Val Val
        115                 120

<210> SEQ ID NO 9

```
<211> LENGTH: 5
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 9

Arg Arg Arg Arg Arg
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 10

Arg Arg Arg Arg Arg Arg
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 11

His His His His His His
1               5

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 12

Lys Asp His Leu Ile His Asn Val His Lys Glu Phe His Ala His Ala
1               5                   10                  15

His Asn Lys

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 13

Asp Tyr Lys Asp Asp Asp Asp Lys
1               5

<210> SEQ ID NO 14
<211> LENGTH: 22
<212> TYPE: PRT
<213> ORGANISM: Artificial Sequence
<220> FEATURE:
<223> OTHER INFORMATION: Description of Artificial Sequence: Synthetic
      amino acid tag
```

```
<400> SEQUENCE: 14

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 15

Ala Trp Arg His Pro Gln Phe Gly Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 16

Trp Ser His Pro Gln Phe Glu Lys
1               5

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 17

Met Asp Val Glu Ala Trp Leu Gly Ala Arg
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 18

Met Asp Val Glu Ala Trp Leu Gly Ala Arg Val Pro Leu Val Glu Thr
1               5                   10                  15

<210> SEQ ID NO 19
<211> LENGTH: 38
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 19

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
```

```
                    20                  25                  30

Gln Gly Gln Arg Glu Pro
            35

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 20

Glu Gln Lys Leu Ile Ser Glu Glu Asp Leu
1               5                   10

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 21

Lys Glu Thr Ala Ala Ala Lys Phe Glu Arg Gln His Met Asp Ser
1               5                   10                  15

<210> SEQ ID NO 22
<211> LENGTH: 26
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 22

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 23
<211> LENGTH: 47
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 23

Pro Ala Thr Thr Thr Gly Ser Ser Pro Gly Pro Thr Gln Ser His Tyr
1               5                   10                  15

Gly Gln Cys Gly Gly Ile Gly Tyr Ser Gly Pro Thr Val Cys Ala Ser
            20                  25                  30

Gly Thr Thr Cys Gln Val Leu Asn Pro Tyr Tyr Ser Gln Cys Leu
        35                  40                  45

<210> SEQ ID NO 24
<211> LENGTH: 32
<212> TYPE: PRT
<213> ORGANISM: Butyrivibrio fibrisolvens

<400> SEQUENCE: 24

Met Asp Trp Asn Ala Asn Ile Ala Pro Gly Asn Ser Val Glu Phe Gly
```

```
                1               5                  10                 15
              Ile Gln Gly Ala Gly Ser Val Gly Asn Val Ile Asp Ile Thr Val Glu
                          20                  25                 30

<210> SEQ ID NO 25
<211> LENGTH: 51
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 25

Thr Asn Pro Gly Val Ser Ala Trp Gln Val Asn Thr Ala Tyr Thr Ala
1               5                  10                  15

Gly Gln Leu Val Thr Tyr Asn Gly Lys Thr Tyr Lys Cys Leu Gln Pro
            20                  25                  30

His Thr Ser Leu Ala Gly Trp Glu Pro Ser Asn Val Pro Ala Leu Trp
        35                  40                  45

Gln Leu Gln
    50

<210> SEQ ID NO 26
<211> LENGTH: 209
<212> TYPE: PRT
<213> ORGANISM: Chondrus crispus

<400> SEQUENCE: 26

Met Pro Glu Ile Lys Leu Thr Tyr Phe Asp Met Arg Gly Arg Ala Glu
1               5                  10                  15

Ala Ser Arg Leu Ala Leu Val Val Gly Glu Ile Pro Phe Glu Asp Glu
            20                  25                  30

Arg Val Val Phe Asp His Trp Lys Glu Ala Lys Pro Lys Thr Pro Tyr
        35                  40                  45

Ala Ala Leu Pro Met Leu Thr Val Asp Gly Met Gln Val Ala Gln Ser
    50                  55                  60

Asp Ala Ile Leu Arg Tyr Cys Gly Lys Leu Ala Gly Leu Tyr Pro Ser
65                  70                  75                  80

Asp Pro Leu Glu Ala Ala Lys Val Asp Glu Val Gly Val Ile Asp
                85                  90                  95

Asp Val Thr His Ala Met Tyr Arg Tyr Arg Gly Asp Asp Lys Asp Lys
            100                 105                 110

Leu Arg Glu Glu Arg Asp Lys Phe Ser Lys Val Asp Val Pro Arg Tyr
        115                 120                 125

Val Gly Ala Leu Glu Lys Arg Leu Glu Ala Phe Gly Asp Gly Pro Trp
    130                 135                 140

Ala Val Gly Gly Asn Met Thr Ile Ala Asp Leu His Ile Cys His Leu
145                 150                 155                 160

Val Thr Asn Ile Arg Cys Gly Met Leu Asp Phe Val Asp Lys Asp Leu
                165                 170                 175

Leu Glu Gly Tyr Val Arg Ile Val Lys Ser Tyr Ser Ala Val Met Glu
            180                 185                 190

His Pro Lys Val Thr Glu Trp Tyr Glu Lys Lys Pro Val Lys Met Phe
        195                 200                 205

Ser

<210> SEQ ID NO 27
```

```
<211> LENGTH: 396
<212> TYPE: PRT
<213> ORGANISM: Escherichia coli

<400> SEQUENCE: 27

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Arg Ile Thr Lys
```

385            390            395

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      protease cleavage site

<400> SEQUENCE: 28

Pro Ala Pro Ser Pro
1               5

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      protease cleavage site

<400> SEQUENCE: 29

Pro Pro Ser Pro
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      protease cleavage site

<400> SEQUENCE: 30

Pro Pro Ala Pro
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      protease cleavage site

<400> SEQUENCE: 31

Pro Pro Thr Pro
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      protease cleavage site

<400> SEQUENCE: 32

Pro Pro Gly Pro
1

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic enzymatic cleavage site

<400> SEQUENCE: 33

Pro Arg Pro Pro Thr Pro
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      enzymatic cleavage site

<400> SEQUENCE: 34

Val Val Ala Pro Pro Ala Pro
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      enzymatic cleavage site

<400> SEQUENCE: 35

Val Val Ala Pro Pro Ser Pro
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      enzymatic cleavage site

<400> SEQUENCE: 36

Val Val Ala Pro Pro Thr Pro
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      enzymatic cleavage site

<400> SEQUENCE: 37

Val Val Ala Pro Pro Gly Pro
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      enzymatic cleavage site

<400> SEQUENCE: 38

Pro Arg Pro Pro Thr Pro
1               5

<210> SEQ ID NO 39

-continued

```
<211> LENGTH: 6
<212> TYPE: PRT
<213> ORGANISM: Artificial Sequence
<220> FEATURE:
<223> OTHER INFORMATION: Description of Artificial Sequence: Synthetic
      enzymatic cleavage site

<400> SEQUENCE: 39

Ala Pro Pro Ala Ala Pro
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      enzymatic cleavage site

<400> SEQUENCE: 40

Pro Arg Pro Pro Ala Pro
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      enzymatic cleavage site

<400> SEQUENCE: 41

Pro Arg Pro Pro Ser Pro
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      enzymatic cleavage site

<400> SEQUENCE: 42

Pro Arg Pro Pro Gly Pro
1               5

<210> SEQ ID NO 43
<211> LENGTH: 285
<212> TYPE: PRT
<213> ORGANISM: Artificial Sequence
<220> FEATURE:
<223> OTHER INFORMATION: Description of Artificial Sequence: Synthetic
      Tetranectin-apolipoprotein A-I (1)

<400> SEQUENCE: 43

Ala Pro Ile Val Asn Ala Lys Lys Asp Val Val Asn Thr Lys Met Phe
1               5                   10                  15

Glu Glu Leu Lys Ser Arg Leu Asp Thr Leu Ala Gln Glu Val Ala Leu
            20                  25                  30

Leu Lys Glu Gln Gln Ala Leu Gln Thr Val Asp Glu Pro Pro Gln Ser
        35                  40                  45

Pro Trp Asp Arg Val Lys Asp Leu Ala Thr Val Tyr Val Asp Val Leu
    50                  55                  60

Lys Asp Ser Gly Arg Asp Tyr Val Ser Gln Phe Glu Gly Ser Ala Leu
65                  70                  75                  80
```

Gly Lys Gln Leu Asn Leu Lys Leu Leu Asp Asn Trp Asp Ser Val Thr
            85                  90                  95

Ser Thr Phe Ser Lys Leu Arg Glu Gln Leu Gly Pro Val Thr Gln Glu
            100                 105                 110

Phe Trp Asp Asn Leu Glu Lys Glu Thr Glu Gly Leu Arg Gln Glu Met
            115                 120                 125

Ser Lys Asp Leu Glu Glu Val Lys Ala Lys Val Gln Pro Tyr Leu Asp
130                 135                 140

Asp Phe Gln Lys Lys Trp Gln Glu Glu Met Glu Leu Tyr Arg Gln Lys
145                 150                 155                 160

Val Glu Pro Leu Arg Ala Glu Leu Gln Glu Gly Ala Arg Gln Lys Leu
                165                 170                 175

His Glu Leu Gln Glu Lys Leu Ser Pro Leu Gly Glu Glu Met Arg Asp
            180                 185                 190

Arg Ala Arg Ala His Val Asp Ala Leu Arg Thr His Leu Ala Pro Tyr
            195                 200                 205

Ser Asp Glu Leu Arg Gln Arg Leu Ala Ala Arg Leu Glu Ala Leu Lys
            210                 215                 220

Glu Asn Gly Gly Ala Arg Leu Ala Glu Tyr His Ala Lys Ala Thr Glu
225                 230                 235                 240

His Leu Ser Thr Leu Ser Glu Lys Ala Lys Pro Ala Leu Glu Asp Leu
            245                 250                 255

Arg Gln Gly Leu Leu Pro Val Leu Glu Ser Phe Lys Val Ser Phe Leu
            260                 265                 270

Ser Ala Leu Glu Glu Tyr Thr Lys Lys Leu Asn Thr Gln
            275                 280                 285

<210> SEQ ID NO 44
<211> LENGTH: 283
<212> TYPE: PRT
<213> ORGANISM: Artificial Sequence
<220> FEATURE:
<223> OTHER INFORMATION: Description of Artificial Sequence: Synthetic
      Tetranectin-apolipoprotein A-I (2)

<400> SEQUENCE: 44

Ile Val Asn Ala Lys Lys Asp Val Val Asn Thr Lys Met Phe Glu Glu
1               5                   10                  15

Leu Lys Ser Arg Leu Asp Thr Leu Ala Gln Glu Val Ala Leu Leu Lys
            20                  25                  30

Glu Gln Gln Ala Leu Gln Thr Val Asp Glu Pro Pro Gln Ser Pro Trp
        35                  40                  45

Asp Arg Val Lys Asp Leu Ala Thr Val Tyr Val Asp Val Leu Lys Asp
    50                  55                  60

Ser Gly Arg Asp Tyr Val Ser Gln Phe Glu Gly Ser Ala Leu Gly Lys
65                  70                  75                  80

Gln Leu Asn Leu Lys Leu Leu Asp Asn Trp Asp Ser Val Thr Ser Thr
            85                  90                  95

Phe Ser Lys Leu Arg Glu Gln Leu Gly Pro Val Thr Gln Glu Phe Trp
            100                 105                 110

Asp Asn Leu Glu Lys Glu Thr Glu Gly Leu Arg Gln Glu Met Ser Lys
            115                 120                 125

Asp Leu Glu Glu Val Lys Ala Lys Val Gln Pro Tyr Leu Asp Asp Phe
130                 135                 140

Gln Lys Lys Trp Gln Glu Glu Met Glu Leu Tyr Arg Gln Lys Val Glu

```
145                 150                 155                 160
Pro Leu Arg Ala Glu Leu Gln Glu Gly Ala Arg Gln Lys Leu His Glu
                165                 170                 175

Leu Gln Glu Lys Leu Ser Pro Leu Gly Glu Glu Met Arg Asp Arg Ala
            180                 185                 190

Arg Ala His Val Asp Ala Leu Arg Thr His Leu Ala Pro Tyr Ser Asp
        195                 200                 205

Glu Leu Arg Gln Arg Leu Ala Ala Arg Leu Glu Ala Leu Lys Glu Asn
    210                 215                 220

Gly Gly Ala Arg Leu Ala Glu Tyr His Ala Lys Ala Thr Glu His Leu
225                 230                 235                 240

Ser Thr Leu Ser Glu Lys Ala Lys Pro Ala Leu Glu Asp Leu Arg Gln
                245                 250                 255

Gly Leu Leu Pro Val Leu Glu Ser Phe Lys Val Ser Phe Leu Ser Ala
            260                 265                 270

Leu Glu Glu Tyr Thr Lys Lys Leu Asn Thr Gln
        275                 280

<210> SEQ ID NO 45
<211> LENGTH: 285
<212> TYPE: PRT
<213> ORGANISM: Artificial Sequence
<220> FEATURE:
<223> OTHER INFORMATION: Description of Artificial Sequence: Synthetic
      Tetranectin-apolipoprotein A-I
<220> FEATURE:
<221> NAME/KEY: MOD_RES
<222> LOCATION: (1)..(1)
<223> OTHER INFORMATION: Ala, Gly, Ser or Thr

<400> SEQUENCE: 45

Xaa Pro Ile Val Asn Ala Lys Lys Asp Val Val Asn Thr Lys Met Phe
1               5                  10                  15

Glu Glu Leu Lys Ser Arg Leu Asp Thr Leu Ala Gln Glu Val Ala Leu
            20                  25                  30

Leu Lys Glu Gln Gln Ala Leu Gln Thr Val Asp Glu Pro Pro Gln Ser
        35                  40                  45

Pro Trp Asp Arg Val Lys Asp Leu Ala Thr Val Tyr Val Asp Val Leu
    50                  55                  60

Lys Asp Ser Gly Arg Asp Tyr Val Ser Gln Phe Glu Gly Ser Ala Leu
65                  70                  75                  80

Gly Lys Gln Leu Asn Leu Lys Leu Leu Asp Asn Trp Asp Ser Val Thr
                85                  90                  95

Ser Thr Phe Ser Lys Leu Arg Glu Gln Leu Gly Pro Val Thr Gln Glu
            100                 105                 110

Phe Trp Asp Asn Leu Glu Lys Glu Thr Glu Gly Leu Arg Gln Glu Met
        115                 120                 125

Ser Lys Asp Leu Glu Glu Val Lys Ala Lys Val Gln Pro Tyr Leu Asp
    130                 135                 140

Asp Phe Gln Lys Lys Trp Gln Glu Glu Met Glu Leu Tyr Arg Gln Lys
145                 150                 155                 160

Val Glu Pro Leu Arg Ala Glu Leu Gln Glu Gly Ala Arg Gln Lys Leu
                165                 170                 175

His Glu Leu Gln Glu Lys Leu Ser Pro Leu Gly Glu Glu Met Arg Asp
            180                 185                 190

Arg Ala Arg Ala His Val Asp Ala Leu Arg Thr His Leu Ala Pro Tyr
        195                 200                 205
```

-continued

```
Ser Asp Glu Leu Arg Gln Arg Leu Ala Ala Arg Leu Glu Ala Leu Lys
    210                 215                 220

Glu Asn Gly Gly Ala Arg Leu Ala Glu Tyr His Ala Lys Ala Thr Glu
225                 230                 235                 240

His Leu Ser Thr Leu Ser Glu Lys Ala Lys Pro Ala Leu Glu Asp Leu
                245                 250                 255

Arg Gln Gly Leu Leu Pro Val Leu Glu Ser Phe Lys Val Ser Phe Leu
                260                 265                 270

Ser Ala Leu Glu Glu Tyr Thr Lys Lys Leu Asn Thr Gln
                275                 280                 285

<210> SEQ ID NO 46
<211> LENGTH: 22
<212> TYPE: PRT
<213> ORGANISM: Artificial Sequence
<220> FEATURE:
<223> OTHER INFORMATION: Description of Artificial Sequence: Synthetic
      Apolipoprotein A-I mimetic (1)

<400> SEQUENCE: 46

Pro Val Leu Asp Glu Phe Arg Glu Lys Leu Asn Glu Glu Leu Glu Ala
1               5                   10                  15

Leu Lys Gln Lys Leu Lys
            20

<210> SEQ ID NO 47
<211> LENGTH: 22
<212> TYPE: PRT
<213> ORGANISM: Artificial Sequence
<220> FEATURE:
<223> OTHER INFORMATION: Description of Artificial Sequence: Synthetic
      Apolipoprotein A-I mimetic (2)

<400> SEQUENCE: 47

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 48
<211> LENGTH: 267
<212> TYPE: PRT
<213> ORGANISM: Homo sapiens

<400> SEQUENCE: 48

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110
```

```
Asp Leu Glu Glu Val Lys Ala Lys Val Gln Pro Tyr Leu Asp Asp Phe
            115                 120                 125

Gln Lys Lys Trp Gln Glu Met Glu Leu Tyr Arg Gln Lys Val Glu
130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265

<210> SEQ ID NO 49
<211> LENGTH: 100
<212> TYPE: PRT
<213> ORGANISM: Homo sapiens

<400> SEQUENCE: 49

Met Lys Leu Leu Ala Ala Thr Val Leu Leu Leu Thr Ile Cys Ser Leu
1               5                   10                  15

Glu Gly Ala Leu Val Arg Arg Gln Ala Lys Glu Pro Cys Val Glu Ser
            20                  25                  30

Leu Val Ser Gln Tyr Phe Gln Thr Val Thr Asp Tyr Gly Lys Asp Leu
        35                  40                  45

Met Glu Lys Val Lys Ser Pro Glu Leu Gln Ala Glu Ala Lys Ser Tyr
    50                  55                  60

Phe Glu Lys Ser Lys Glu Gln Leu Thr Pro Leu Ile Lys Lys Ala Gly
65                  70                  75                  80

Thr Glu Leu Val Asn Phe Leu Ser Tyr Phe Val Glu Leu Gly Thr Gln
                85                  90                  95

Pro Ala Thr Gln
            100

<210> SEQ ID NO 50
<211> LENGTH: 396
<212> TYPE: PRT
<213> ORGANISM: Homo sapiens

<400> SEQUENCE: 50

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60
```

-continued

Lys Leu Gly Glu Val Asn Thr Tyr Ala Gly Asp Leu Gln Lys Lys Leu
 65                  70                  75                  80

Val Pro Phe Ala Thr Glu Leu His Glu Arg Leu Ala Lys Asp Ser Glu
                 85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Thr Pro Tyr
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Arg Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
    370                 375                 380

Gln Glu Gln Val Gln Met Leu Ala Pro Leu Glu Ser
385                 390                 395

<210> SEQ ID NO 51
<211> LENGTH: 366
<212> TYPE: PRT
<213> ORGANISM: Homo sapiens

<400> SEQUENCE: 51

Met Ala Ser Met Ala Ala Val Leu Thr Trp Ala Leu Ala Leu Leu Ser
 1               5                  10                  15

Ala Phe Ser Ala Thr Gln Ala Arg Lys Gly Phe Trp Asp Tyr Phe Ser
                20                  25                  30

Gln Thr Ser Gly Asp Lys Gly Arg Val Glu Gln Ile His Gln Gln Lys
            35                  40                  45

Met Ala Arg Glu Pro Ala Thr Leu Lys Asp Ser Leu Glu Gln Asp Leu
    50                  55                  60

Asn Asn Met Asn Lys Phe Leu Glu Lys Leu Arg Pro Leu Ser Gly Ser
65                  70                  75                  80

Glu Ala Pro Arg Leu Pro Gln Asp Pro Val Gly Met Arg Arg Gln Leu
                85                  90                  95

Gln Glu Glu Leu Glu Glu Val Lys Ala Arg Leu Gln Pro Tyr Met Ala
            100                 105                 110

Glu Ala His Glu Leu Val Gly Trp Asn Leu Glu Gly Leu Arg Gln Gln
        115                 120                 125

Leu Lys Pro Tyr Thr Met Asp Leu Met Glu Gln Val Ala Leu Arg Val
    130                 135                 140

Gln Glu Leu Gln Glu Gln Leu Arg Val Val Gly Glu Asp Thr Lys Ala
145                 150                 155                 160

Gln Leu Leu Gly Gly Val Asp Glu Ala Trp Ala Leu Leu Gln Gly Leu
                165                 170                 175

Gln Ser Arg Val Val His His Thr Gly Arg Phe Lys Glu Leu Phe His
            180                 185                 190

Pro Tyr Ala Glu Ser Leu Val Ser Gly Ile Gly Arg His Val Gln Glu
        195                 200                 205

Leu His Arg Ser Val Ala Pro His Ala Pro Ala Ser Pro Ala Arg Leu
    210                 215                 220

Ser Arg Cys Val Gln Val Leu Ser Arg Lys Leu Thr Leu Lys Ala Lys
225                 230                 235                 240

Ala Leu His Ala Arg Ile Gln Gln Asn Leu Asp Gln Leu Arg Glu Glu
                245                 250                 255

Leu Ser Arg Ala Phe Ala Gly Thr Gly Thr Glu Glu Gly Ala Gly Pro
            260                 265                 270

Asp Pro Gln Met Leu Ser Glu Glu Val Arg Gln Arg Leu Gln Ala Phe
        275                 280                 285

Arg Gln Asp Thr Tyr Leu Gln Ile Ala Ala Phe Thr Arg Ala Ile Asp
    290                 295                 300

Gln Glu Thr Glu Glu Val Gln Gln Gln Leu Ala Pro Pro Pro Pro Gly
305                 310                 315                 320

His Ser Ala Phe Ala Pro Glu Phe Gln Gln Thr Asp Ser Gly Lys Val
                325                 330                 335

Leu Ser Lys Leu Gln Ala Arg Leu Asp Asp Leu Trp Glu Asp Ile Thr
            340                 345                 350

His Ser Leu His Asp Gln Gly His Ser His Leu Gly Asp Pro
        355                 360                 365

<210> SEQ ID NO 52
<211> LENGTH: 267
<212> TYPE: PRT
<213> ORGANISM: Homo sapiens

<400> SEQUENCE: 52

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys

```
                50                  55                  60
Gln Leu Asn Leu Lys Leu Leu Asp Asn Trp Asp Ser Val Thr Ser Thr
 65                  70                  75                  80

Phe Ser Lys Leu Arg Glu Gln Leu Gly Pro Val Thr Gln Glu Phe Trp
                 85                  90                  95

Asp Asn Leu Glu Lys Glu Thr Glu Gly Leu Arg Gln Glu Met Ser Lys
                100                 105                 110

Asp Leu Glu Glu Val Lys Ala Lys Val Gln Pro Tyr Leu Asp Asp Phe
                115                 120                 125

Gln Lys Lys Trp Gln Glu Glu Met Glu Leu Tyr Arg Gln Lys Val Glu
            130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Met Arg Asp Arg Ala
                165                 170                 175

Arg Ala His Val Asp Ala Leu Arg Thr His Leu Ala Pro Tyr Ser Asp
                180                 185                 190

Glu Leu Arg Gln Arg Leu Ala Ala Arg Leu Glu Ala Leu Lys Glu Asn
                195                 200                 205

Gly Gly Ala Arg Leu Ala Glu Tyr His Ala Lys Ala Thr Glu His Leu
210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
                260                 265

<210> SEQ ID NO 53
<211> LENGTH: 267
<212> TYPE: PRT
<213> ORGANISM: Homo sapiens

<400> SEQUENCE: 53

Met Lys Ala Ala Val Leu Thr Leu Ala Val Leu Phe Leu Thr Gly Ser
 1               5                  10                  15

Gln Ala Arg His Phe Trp Gln Gln Asp Glu Pro Gln Ser Pro Trp
                 20                  25                  30                 Trp

Asp Arg Val Lys Asp Leu Ala Thr Val Tyr Val Asp Val Leu Lys Asp
                 35                  40                  45

Ser Gly Arg Asp Tyr Val Ser Gln Phe Glu Gly Ser Ala Leu Gly Lys
 50                  55                  60

Gln Leu Asn Leu Lys Leu Leu Asp Asn Trp Asp Ser Val Thr Ser Thr
 65                  70                  75                  80

Phe Ser Lys Leu Arg Glu Gln Leu Gly Pro Val Thr Gln Glu Phe Trp
                 85                  90                  95

Asp Asn Leu Glu Lys Glu Thr Glu Gly Leu Arg Gln Glu Met Ser Lys
                100                 105                 110

Asp Leu Glu Glu Val Lys Ala Lys Val Gln Pro Tyr Leu Asp Asp Phe
                115                 120                 125

Gln Lys Lys Trp Gln Glu Glu Met Glu Leu Tyr Arg Gln Lys Val Glu
            130                 135                 140

Pro Leu Arg Ala Glu Leu Gln Glu Gly Ala Arg Gln Lys Leu His Glu
145                 150                 155                 160
```

```
Leu Gln Glu Lys Leu Ser Pro Leu Gly Glu Met Arg Asp Arg Ala
            165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265

<210> SEQ ID NO 54
<211> LENGTH: 267
<212> TYPE: PRT
<213> ORGANISM: Homo sapiens

<400> SEQUENCE: 54

Met Lys Ala Thr Val Leu Thr Leu Ala Val Leu Phe Leu Thr Gly Ser
1               5                   10                  15

Gln Ala Arg His Phe Trp Gln Gln Asp Glu Pro Pro Gln Thr Pro Trp
            20                  25                  30

Asp Arg Val Lys Asp Leu Val Thr Val Tyr Val Glu Ala Leu Lys Asp
        35                  40                  45

Ser Gly Lys Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Val Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu His Glu Gly Thr Arg Gln Lys Leu His Glu
145                 150                 155                 160

Leu His Glu Lys Leu Ser Pro Leu Gly Glu Glu Val Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Ser Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Ser Thr Gln
            260                 265
```

```
<210> SEQ ID NO 55
<211> LENGTH: 265
<212> TYPE: PRT
<213> ORGANISM: Homo sapiens

<400> SEQUENCE: 55

Met Lys Ala Val Val Leu Thr Leu Ala Val Leu Phe Leu Thr Gly Ser
1               5                   10                  15

Gln Ala Arg His Phe Trp Gln Gln Asp Asp Pro Gln Ser Ser Trp Asp
            20                  25                  30

Arg Val Lys Asp Phe Ala Thr Val Tyr Val Glu Ala Ile Lys Asp Ser
        35                  40                  45

Gly Arg Asp Tyr Val Ala Gln Phe Glu Ala Ser Ala Leu Gly Lys Gln
    50                  55                  60

Leu Asn Leu Lys Leu Leu Asp Asn Trp Asp Thr Leu Ala Ser Thr Leu
65                  70                  75                  80

Ser Lys Val Arg Glu Gln Leu Gly Pro Val Thr Gln Glu Phe Trp Asp
                85                  90                  95

Asn Leu Glu Lys Glu Thr Ala Ser Leu Arg Gln Glu Met His Lys Asp
            100                 105                 110

Leu Glu Glu Val Lys Gln Lys Val Gln Pro Tyr Leu Asp Glu Phe Gln
        115                 120                 125

Lys Lys Trp His Glu Glu Val Glu Ile Tyr Arg Gln Lys Val Ala Pro
    130                 135                 140

Leu Gly Glu Glu Phe Arg Glu Gly Ala Arg Gln Lys Val Gln Glu Leu
145                 150                 155                 160

Gln Asp Lys Leu Ser Pro Leu Ala Gln Glu Leu Arg Asp Arg Ala Arg
                165                 170                 175

Ala His Val Glu Thr Leu Arg Gln Gln Leu Ala Pro Tyr Ser Asp Asp
            180                 185                 190

Leu Arg Gln Arg Leu Thr Ala Arg Leu Glu Ala Leu Lys Glu Gly Gly
        195                 200                 205

Gly Ser Leu Ala Glu Tyr His Ala Lys Ala Ser Glu Gln Leu Lys Ala
    210                 215                 220

Leu Gly Glu Lys Ala Lys Pro Val Leu Glu Asp Leu Arg Gln Gly Leu
225                 230                 235                 240

Leu Pro Val Leu Glu Ser Leu Lys Val Ser Ile Leu Ala Ala Ile Asp
                245                 250                 255

Glu Ala Ser Lys Lys Leu Asn Ala Gln
            260                 265

<210> SEQ ID NO 56
<211> LENGTH: 264
<212> TYPE: PRT
<213> ORGANISM: Homo sapiens

<400> SEQUENCE: 56

Met Lys Ala Trp Leu Thr Leu Ala Val Leu Phe Leu Thr Gly Ser Gln
1               5                   10                  15

Ala Arg His Phe Trp Gln Gln Asp Asp Pro Gln Ser Pro Trp Asp Arg
            20                  25                  30

Val Lys Asp Phe Ala Thr Val Tyr Val Asp Ala Ile Lys Asp Ser Gly
        35                  40                  45

Arg Asp Tyr Val Ala Gln Phe Glu Ala Ser Ala Leu Gly Lys His Leu
    50                  55                  60
```

-continued

Asn Leu Lys Leu Leu Asp Asn Trp Asp Ser Leu Gly Ser Thr Phe Thr
65                  70                  75                  80

Lys Val Arg Glu Gln Leu Gly Pro Val Thr Gln Glu Phe Trp Asp Asn
            85                  90                  95

Leu Glu Lys Glu Thr Glu Ala Leu Arg Gln Glu Met Ser Lys Asp Leu
        100                 105                 110

Glu Glu Val Lys Lys Val Gln Pro Tyr Leu Asp Asp Phe Gln Asn
        115                 120                 125

Lys Trp Gln Glu Glu Met Glu Thr Tyr Arg Gln Lys Met Ala Pro Leu
130                 135                 140

Gly Ala Glu Phe Arg Glu Gly Ala Arg Gln Lys Val Gln Glu Leu Gln
145                 150                 155                 160

Glu Lys Leu Ser Pro Leu Ala Glu Glu Leu Arg Asp Arg Leu Arg Ala
                165                 170                 175

His Val Glu Ala Leu Arg Gln His Val Ala Pro Tyr Ser Asp Asp Leu
            180                 185                 190

Arg Gln Arg Met Ala Ala Arg Phe Glu Ala Leu Lys Glu Gly Gly Gly
        195                 200                 205

Ser Leu Ala Glu Tyr Gln Ala Lys Ala Gln Gln Leu Lys Ala Leu
210                 215                 220

Gly Glu Lys Ala Lys Pro Ala Leu Glu Asp Leu Arg Gln Gly Leu Leu
225                 230                 235                 240

Pro Val Leu Glu Asn Leu Lys Val Ser Ile Leu Ala Ala Ile Asp Glu
                245                 250                 255

Ala Ser Lys Lys Leu Asn Ala Gln
            260

<210> SEQ ID NO 57
<211> LENGTH: 266
<212> TYPE: PRT
<213> ORGANISM: Homo sapiens

<400> SEQUENCE: 57

Met Lys Ala Ala Leu Leu Thr Leu Ala Val Leu Phe Leu Thr Gly Ser
1               5                   10                  15

Gln Ala Arg His Phe Trp Gln Asp Glu Pro Gln Ser Pro Trp Asp
            20                  25                  30

Arg Val Lys Asp Leu Ala Thr Val Tyr Val Asp Ala Val Lys Asp Ser
            35                  40                  45

Gly Arg Asp Tyr Val Ala Gln Phe Glu Ala Ser Ala Leu Gly Lys Gln
50                  55                  60

Leu Asn Leu Lys Leu Leu Asp Asn Trp Asp Ser Leu Ser Ser Thr Val
65                  70                  75                  80

Thr Lys Leu Arg Glu Gln Ile Gly Pro Val Thr Gln Glu Phe Trp Asp
            85                  90                  95

Asn Leu Glu Lys Glu Thr Glu Val Leu Arg Gln Glu Met Ser Lys Asp
        100                 105                 110

Leu Glu Glu Val Lys Gln Lys Val Gln Pro Tyr Leu Asp Asp Phe Gln
        115                 120                 125

Lys Lys Trp Gln Glu Glu Val Glu Leu Tyr Arg Gln Lys Val Ala Pro
130                 135                 140

Leu Gly Ser Glu Leu Arg Glu Gly Ala Arg Gln Lys Leu Gln Glu Leu
145                 150                 155                 160

Gln Glu Lys Leu Ser Pro Leu Ala Glu Glu Leu Arg Asp Arg Ala Arg

```
                    165                 170                 175

Thr His Val Asp Ala Leu Arg Ala Gln Leu Ala Pro Tyr Ser Asp Asp
                180                 185                 190

Leu Arg Glu Arg Leu Ala Ala Arg Leu Glu Ala Leu Lys Glu Gly Gly
            195                 200                 205

Gly Ala Ser Leu Ala Glu Tyr His Ala Arg Ala Ser Glu Gln Leu Ser
        210                 215                 220

Ala Leu Gly Glu Lys Ala Arg Pro Ala Leu Glu Asp Leu Arg Gln Gly
225                 230                 235                 240

Leu Leu Pro Val Leu Glu Ser Phe Lys Val Ser Leu Leu Ala Ala Ile
                245                 250                 255

Asp Glu Ala Thr Lys Lys Leu Asn Ala Gln
                260                 265

<210> SEQ ID NO 58
<211> LENGTH: 206
<212> TYPE: PRT
<213> ORGANISM: Homo sapiens

<400> SEQUENCE: 58

Met Lys Ala Val Val Leu Thr Leu Ala Val Leu Phe Leu Thr Gly Ser
1               5                   10                  15

Gln Ala Arg His Phe Trp Gln Arg Asp Glu Pro Arg Ser Ser Trp Asp
            20                  25                  30

Lys Ile Lys Asp Phe Ala Thr Val Tyr Val Asp Thr Val Lys Asp Ser
        35                  40                  45

Gly Arg Glu Tyr Val Ala Gln Phe Glu Ala Ser Ala Phe Gly Lys Gln
    50                  55                  60

Leu Asn Leu Lys Leu Leu Asp Asn Trp Asp Ser Leu Ser Ser Thr Val
65                  70                  75                  80

Ser Lys Leu Gln Glu Gln Leu Gly Pro Val Thr Gln Glu Phe Trp Asp
                85                  90                  95

Asn Leu Glu Lys Glu Thr Glu Gly Leu Arg Glu Glu Met Asn Lys Asp
            100                 105                 110

Leu Gln Glu Val Arg Gln Lys Val Gln Pro Tyr Leu Asp Glu Phe Gln
        115                 120                 125

Lys Lys Trp Gln Glu Glu Val Glu Arg Tyr Arg Gln Lys Val Glu Pro
    130                 135                 140

Leu Gly Ala Glu Leu Arg Glu Ser Ala Arg Gln Lys Leu Thr Glu Leu
145                 150                 155                 160

Gln Glu Lys Leu Ser Pro Leu Ala Glu Glu Leu Arg Asp Ser Ala Arg
                165                 170                 175

Thr His Val Gly Leu Leu Pro Val Leu Glu Ser Phe Lys Ala Ser Val
                180                 185                 190

Gln Asn Val Leu Asp Glu Ala Thr Lys Lys Leu Asn Thr Gln
            195                 200                 205

<210> SEQ ID NO 59
<211> LENGTH: 265
<212> TYPE: PRT
<213> ORGANISM: Homo sapiens

<400> SEQUENCE: 59

Met Lys Ala Val Val Leu Thr Leu Ala Val Leu Phe Leu Thr Gly Ser
1               5                   10                  15

Gln Ala Arg His Phe Trp Gln Gln Asp Glu Pro Gln Ser Ser Trp Asp
```

```
            20                  25                  30
Arg Val Arg Asp Leu Ala Asn Val Tyr Val Asp Ala Val Lys Glu Ser
        35                  40                  45

Gly Arg Glu Tyr Val Ser Gln Leu Glu Ala Ser Ala Leu Gly Lys Gln
    50                  55                  60

Leu Asn Leu Lys Leu Val Asp Asn Trp Asp Thr Leu Gly Ser Thr Phe
65                  70                  75                  80

Gln Lys Val His Glu His Leu Gly Pro Val Ala Gln Glu Phe Trp Glu
                85                  90                  95

Lys Leu Glu Lys Glu Thr Glu Leu Arg Arg Glu Ile Asn Lys Asp
            100                 105                 110

Leu Glu Asp Val Arg Gln Lys Thr Gln Pro Phe Leu Asp Glu Ile Gln
        115                 120                 125

Lys Lys Trp Gln Glu Asp Leu Glu Arg Tyr Arg Gln Lys Val Glu Pro
    130                 135                 140

Leu Ser Ala Gln Leu Arg Glu Gly Ala Arg Gln Lys Leu Met Glu Leu
145                 150                 155                 160

Gln Glu Gln Val Thr Pro Leu Gly Glu Asp Leu Arg Asp Ser Val Arg
                165                 170                 175

Ala Tyr Ala Asp Thr Leu Arg Thr Gln Leu Ala Pro Tyr Ser Glu Gln
            180                 185                 190

Met Arg Lys Thr Leu Gly Ala Arg Leu Glu Ala Ile Lys Glu Gly Gly
        195                 200                 205

Ser Ala Ser Leu Ala Glu Tyr His Ala Lys Ala Ser Glu Gln Leu Ser
    210                 215                 220

Ala Leu Gly Glu Lys Ala Lys Pro Val Leu Glu Asp Ile His Gln Gly
225                 230                 235                 240

Leu Met Pro Met Trp Glu Ser Phe Lys Thr Gly Val Leu Asn Val Ile
                245                 250                 255

Asp Glu Ala Ala Lys Lys Leu Thr Ala
            260                 265

<210> SEQ ID NO 60
<211> LENGTH: 264
<212> TYPE: PRT
<213> ORGANISM: Homo sapiens

<400> SEQUENCE: 60

Met Lys Ala Val Val Leu Ala Val Ala Leu Val Phe Leu Thr Gly Ser
1               5                   10                  15

Gln Ala Trp His Val Trp Gln Gln Glu Pro Gln Ser Gln Trp Asp
                20                  25                  30

Lys Val Lys Asp Phe Ala Asn Val Tyr Val Asp Ala Val Lys Asp Ser
        35                  40                  45

Gly Arg Asp Tyr Val Ser Gln Phe Glu Ser Ser Leu Gly Gln Gln
    50                  55                  60

Leu Asn Leu Asn Leu Leu Glu Asn Trp Asp Thr Leu Gly Ser Thr Val
65                  70                  75                  80

Ser Gln Leu Gln Glu Arg Leu Gly Pro Leu Thr Arg Asp Phe Trp Asp
                85                  90                  95

Asn Leu Glu Lys Glu Thr Asp Trp Val Arg Gln Glu Met Asn Lys Asp
            100                 105                 110

Leu Glu Glu Val Lys Gln Lys Val Gln Pro Tyr Leu Asp Glu Phe Gln
        115                 120                 125
```

```
Lys Lys Trp Lys Glu Asp Val Glu Leu Tyr Arg Gln Lys Val Ala Pro
    130                 135                 140
Leu Gly Ala Glu Leu Gln Glu Ser Ala Arg Gln Lys Leu Gln Glu Leu
145                 150                 155                 160
Gln Gly Arg Leu Ser Pro Val Ala Glu Glu Phe Arg Asp Arg Met Arg
                165                 170                 175
Thr His Val Asp Ser Leu Arg Thr Gln Leu Ala Pro His Ser Glu Gln
            180                 185                 190
Met Arg Glu Ser Leu Ala Gln Arg Leu Ala Glu Leu Lys Ser Asn Pro
        195                 200                 205
Thr Leu Asn Glu Tyr His Thr Arg Ala Lys Thr His Leu Lys Thr Leu
    210                 215                 220
Gly Glu Lys Ala Arg Pro Ala Leu Glu Asp Leu Arg His Ser Leu Met
225                 230                 235                 240
Pro Met Leu Glu Thr Leu Lys Thr Lys Ala Gln Ser Val Ile Asp Lys
                245                 250                 255
Ala Ser Glu Thr Leu Thr Ala Gln
            260

<210> SEQ ID NO 61
<211> LENGTH: 259
<212> TYPE: PRT
<213> ORGANISM: Homo sapiens

<400> SEQUENCE: 61

Met Lys Ala Ala Val Leu Ala Val Ala Leu Val Phe Leu Thr Gly Cys
1               5                   10                  15
Gln Ala Trp Glu Phe Trp Gln Gln Asp Glu Pro Gln Ser Gln Trp Asp
                20                  25                  30
Arg Val Lys Asp Phe Ala Thr Val Tyr Val Asp Ala Val Lys Asp Ser
            35                  40                  45
Gly Arg Asp Tyr Val Ser Gln Phe Glu Ser Ser Thr Leu Gly Lys Gln
        50                  55                  60
Leu Asn Leu Asn Leu Leu Asp Asn Trp Asp Thr Leu Gly Ser Thr Val
65                  70                  75                  80
Gly Arg Leu Gln Glu Gln Leu Gly Pro Val Thr Gln Glu Phe Trp Ala
                85                  90                  95
Asn Leu Glu Lys Glu Thr Asp Trp Leu Arg Asn Glu Met Asn Lys Asp
                100                 105                 110
Leu Glu Asn Val Lys Gln Lys Met Gln Pro His Leu Asp Glu Phe Gln
            115                 120                 125
Glu Lys Trp Asn Glu Glu Val Glu Ala Tyr Arg Gln Lys Leu Glu Pro
        130                 135                 140
Leu Gly Thr Glu Leu His Lys Asn Ala Lys Glu Met Gln Arg His Leu
145                 150                 155                 160
Lys Val Val Ala Glu Glu Phe Arg Asp Arg Met Arg Val Asn Ala Asp
                165                 170                 175
Ala Leu Arg Ala Lys Phe Gly Leu Tyr Ser Asp Gln Met Arg Glu Asn
            180                 185                 190
Leu Ala Gln Arg Leu Thr Glu Ile Arg Asn His Pro Thr Leu Ile Glu
        195                 200                 205
Tyr His Thr Lys Ala Gly Asp His Leu Arg Thr Leu Gly Glu Lys Ala
    210                 215                 220
Lys Pro Ala Leu Asp Asp Leu Gly Gln Gly Leu Met Pro Val Leu Glu
225                 230                 235                 240
```

```
Ala Trp Lys Ala Lys Ile Met Ser Met Ile Asp Glu Ala Lys Lys
                245                 250                 255

Leu Asn Ala

<210> SEQ ID NO 62
<211> LENGTH: 241
<212> TYPE: PRT
<213> ORGANISM: Homo sapiens

<400> SEQUENCE: 62

Asp Glu Ala Lys Ser Tyr Trp Asp Gln Ile Lys Asp Met Leu Thr Val
1               5                   10                  15

Tyr Val Asp Thr Ala Lys Asp Ser Gly Lys Asp Tyr Leu Thr Ser Leu
            20                  25                  30

Asp Thr Ser Ala Leu Gly Gln Gln Leu Asn Lys Lys Leu Ala Asp Asn
        35                  40                  45

Trp Asp Thr Val Ser Ser Ala Leu Leu Lys Ala Arg Glu Gln Met Lys
50                  55                  60

Pro Ile Ala Met Glu Phe Trp Gly Asn Leu Glu Lys Asp Thr Glu Gly
65                  70                  75                  80

Leu Arg Gln Thr Val Ser Lys Asp Leu Glu Leu Val Lys Glu Lys Val
                85                  90                  95

Gln Pro Tyr Leu Asp Ser Phe Lys Lys Val Glu Glu Leu Glu
            100                 105                 110

Leu Tyr Arg Gln Lys Val Ala Pro Leu Ser Ala Glu Trp Arg Glu Gln
        115                 120                 125

Ala Arg Gln Lys Ala Gln Glu Leu Gln Gln Lys Ala Gly Glu Leu Gly
130                 135                 140

Gln Gln His Arg Asp Arg Val Arg Thr His Val Asp Ala Leu Arg Thr
145                 150                 155                 160

Asp Leu Ala Pro Tyr Gly Glu Glu Ala Arg Lys Leu Leu Gln Arg
                165                 170                 175

Leu Gln Asp Ile Lys Ala Lys Ser Gly Asp Leu Ala Glu Tyr Gln Thr
        180                 185                 190

Lys Leu Ser Glu His Leu Lys Ser Phe Gly Glu Lys Ala Gln Pro Thr
    195                 200                 205

Leu Gln Asp Leu Arg His Gly Leu Glu Pro Leu Trp Glu Gly Ile Lys
210                 215                 220

Ala Gly Ala Met Ser Met Leu Glu Glu Leu Gly Lys Lys Leu Asn Ser
225                 230                 235                 240

Gln

<210> SEQ ID NO 63
<211> LENGTH: 264
<212> TYPE: PRT
<213> ORGANISM: Homo sapiens

<400> SEQUENCE: 63

Met Arg Gly Val Leu Val Thr Leu Ala Val Leu Phe Leu Thr Gly Thr
1               5                   10                  15

Gln Ala Arg Ser Phe Trp Gln His Asp Glu Pro Gln Thr Pro Leu Asp
            20                  25                  30

Arg Ile Arg Asp Met Val Asp Val Tyr Leu Glu Thr Val Lys Ala Ser
        35                  40                  45

Gly Lys Asp Ala Ile Ala Gln Phe Glu Ser Ser Ala Val Gly Lys Gln
```

```
            50                  55                  60
Leu Asp Leu Lys Leu Ala Asp Asn Leu Asp Thr Leu Ser Ala Ala Ala
 65                  70                  75                  80

Ala Lys Leu Arg Glu Asp Met Ala Pro Tyr Tyr Lys Glu Val Arg Glu
                 85                  90                  95

Met Trp Leu Lys Asp Thr Glu Ala Leu Arg Ala Glu Leu Thr Lys Asp
                100                 105                 110

Leu Glu Glu Val Lys Glu Lys Ile Arg Pro Phe Leu Asp Gln Phe Ser
            115                 120                 125

Ala Lys Trp Thr Glu Glu Leu Glu Gln Tyr Arg Gln Arg Leu Thr Pro
        130                 135                 140

Val Ala Gln Glu Leu Lys Glu Leu Thr Lys Gln Lys Val Glu Leu Met
145                 150                 155                 160

Gln Ala Lys Leu Thr Pro Val Ala Glu Glu Ala Arg Asp Arg Leu Arg
                165                 170                 175

Gly His Val Glu Glu Leu Arg Lys Asn Leu Ala Pro Tyr Ser Asp Glu
                180                 185                 190

Leu Arg Gln Lys Leu Ser Gln Lys Leu Glu Glu Ile Arg Glu Lys Gly
            195                 200                 205

Ile Pro Gln Ala Ser Glu Tyr Gln Ala Lys Val Met Glu Gln Leu Ser
210                 215                 220

Asn Leu Arg Glu Lys Met Thr Pro Leu Val Gln Glu Phe Arg Glu Arg
225                 230                 235                 240

Leu Thr Pro Tyr Ala Glu Asn Leu Lys Asn Arg Leu Ile Ser Phe Leu
                245                 250                 255

Asp Glu Leu Gln Lys Ser Val Ala
            260

<210> SEQ ID NO 64
<211> LENGTH: 264
<212> TYPE: PRT
<213> ORGANISM: Homo sapiens

<400> SEQUENCE: 64

Met Arg Gly Val Leu Val Thr Leu Ala Val Leu Phe Leu Thr Gly Thr
 1               5                  10                  15

Gln Ala Arg Ser Phe Trp Gln His Asp Asp Pro Gln Thr Pro Leu Asp
                20                  25                  30

Arg Ile Arg Asp Met Leu Asp Val Tyr Leu Glu Thr Val Lys Ala Ser
            35                  40                  45

Gly Lys Asp Ala Ile Ser Gln Phe Glu Ser Ser Ala Val Gly Lys Gln
        50                  55                  60

Leu Asp Leu Lys Leu Ala Asp Asn Leu Asp Thr Leu Ser Ala Ala Ala
 65                  70                  75                  80

Ala Lys Leu Arg Glu Asp Met Thr Pro Tyr Tyr Arg Glu Val Arg Glu
                85                  90                  95

Met Trp Leu Lys Asp Thr Glu Ala Leu Arg Ala Glu Leu Thr Lys Asp
                100                 105                 110

Leu Glu Glu Val Lys Glu Lys Ile Arg Pro Phe Leu Asp Gln Phe Ser
            115                 120                 125

Ala Lys Trp Thr Glu Glu Val Glu Gln Tyr Arg Gln Arg Leu Ala Pro
        130                 135                 140

Val Ala Gln Glu Leu Lys Asp Leu Thr Lys Gln Lys Val Glu Leu Met
145                 150                 155                 160
```

```
Gln Ala Lys Leu Thr Pro Val Ala Glu Glu Val Arg Asp Arg Leu Arg
            165                 170                 175

Glu Gln Val Glu Glu Leu Arg Lys Asn Leu Ala Pro Tyr Ser Ser Glu
        180                 185                 190

Leu Arg Gln Lys Leu Ser Gln Lys Leu Glu Glu Ile Arg Glu Arg Gly
        195                 200                 205

Ile Pro Gln Ala Ser Glu Tyr Gln Ala Lys Val Val Glu Gln Leu Ser
210                 215                 220

Asn Leu Arg Glu Lys Met Thr Pro Leu Val Gln Glu Phe Lys Glu Arg
225                 230                 235                 240

Leu Thr Pro Tyr Ala Glu Asn Leu Lys Asn Arg Leu Ile Asp Leu Leu
        245                 250                 255

Asp Glu Val Gln Lys Thr Met Ala
            260

<210> SEQ ID NO 65
<211> LENGTH: 264
<212> TYPE: PRT
<213> ORGANISM: Homo sapiens

<400> SEQUENCE: 65

Met Arg Val Val Val Thr Leu Ala Leu Leu Phe Leu Thr Gly Thr
1               5                   10                  15

Gln Ala Arg Tyr Phe Trp Gln His Asp Glu Pro Gln Ala Pro Leu Asp
            20                  25                  30

Arg Leu Arg Asp Leu Val Asp Val Tyr Leu Glu Thr Val Lys Ala Ser
        35                  40                  45

Gly Lys Asp Ala Ile Ala Gln Phe Glu Ala Ser Ala Val Gly Lys Gln
50                  55                  60

Leu Asp Leu Lys Leu Ala Asp Asn Leu Asp Thr Leu Gly Ala Ala Ala
65                  70                  75                  80

Ala Lys Leu Arg Glu Asp Met Ala Pro Tyr Tyr Lys Glu Val Arg Glu
            85                  90                  95

Met Trp Leu Lys Asp Thr Glu Ser Leu Arg Ala Glu Leu Thr Lys Asp
            100                 105                 110

Leu Glu Glu Val Lys Glu Lys Ile Arg Pro Phe Leu Asp Gln Phe Ser
        115                 120                 125

Ala Lys Trp Thr Glu Glu Leu Glu Gln Tyr Arg Gln Arg Leu Ala Pro
130                 135                 140

Val Ala Glu Glu Leu Lys Glu Leu Thr Lys Gln Lys Val Glu Leu Met
145                 150                 155                 160

Gln Gln Lys Leu Thr Pro Val Ala Glu Glu Ala Arg Asp Arg Leu Arg
            165                 170                 175

Gly His Val Glu Glu Leu Arg Lys Asn Leu Ala Pro Tyr Ser Asp Glu
        180                 185                 190

Leu Arg Gln Lys Leu Ser Gln Lys Leu Glu Glu Ile Arg Glu Lys Gly
        195                 200                 205

Ile Pro Gln Ala Ala Glu Tyr Gln Ala Lys Val Val Glu Gln Leu Ser
210                 215                 220

Asn Leu Arg Glu Lys Met Thr Pro Leu Val Gln Asp Phe Lys Glu Arg
225                 230                 235                 240

Leu Thr Pro Tyr Ala Glu Asn Leu Lys Thr Arg Phe Ile Ser Leu Leu
        245                 250                 255

Asp Glu Leu Gln Lys Thr Val Ala
            260
```

<210> SEQ ID NO 66
<211> LENGTH: 262
<212> TYPE: PRT
<213> ORGANISM: Homo sapiens

<400> SEQUENCE: 66

Met Lys Phe Leu Ala Leu Ala Leu Thr Ile Leu Leu Ala Ala Gly Thr
1               5                   10                  15

Gln Ala Phe Pro Met Gln Ala Asp Ala Pro Ser Gln Leu Glu His Val
                20                  25                  30

Lys Ala Ala Leu Ser Met Tyr Ile Ala Gln Val Lys Leu Thr Ala Gln
            35                  40                  45

Arg Ser Ile Asp Leu Leu Asp Asp Thr Glu Tyr Lys Glu Tyr Lys Met
        50                  55                  60

Gln Leu Thr Gln Ser Leu Asp Asn Leu Gln Gln Tyr Ala Asp Ala Thr
65                  70                  75                  80

Ser Gln Ser Leu Ala Pro Tyr Ser Glu Ala Phe Gly Thr Gln Leu Thr
                85                  90                  95

Asp Ala Thr Ala Ala Val Arg Ala Glu Val Met Lys Asp Val Glu Glu
            100                 105                 110

Leu Arg Ser Gln Leu Glu Pro Lys Arg Ala Glu Leu Lys Glu Val Leu
        115                 120                 125

Asp Lys His Ile Asp Glu Tyr Arg Lys Lys Leu Glu Pro Leu Ile Lys
    130                 135                 140

Glu His Ile Glu Leu Arg Arg Thr Glu Met Glu Ala Phe Arg Ala Lys
145                 150                 155                 160

Met Glu Pro Ile Val Glu Glu Leu Arg Ala Lys Val Ala Ile Asn Val
                165                 170                 175

Glu Glu Thr Lys Thr Lys Leu Met Pro Ile Val Glu Ile Val Arg Ala
            180                 185                 190

Lys Leu Thr Glu Arg Leu Glu Glu Leu Arg Thr Leu Ala Ala Pro Tyr
        195                 200                 205

Ala Glu Glu Tyr Lys Val Gln Met Ile Lys Ala Val Gly Glu Val Arg
    210                 215                 220

Glu Lys Val Ser Pro Leu Ser Glu Asp Phe Lys Gly Gln Val Gly Pro
225                 230                 235                 240

Ala Ala Glu Gln Ala Lys Gln Lys Leu Leu Ala Phe Tyr Glu Thr Ile
                245                 250                 255

Ser Gln Ala Met Lys Ala
            260

<210> SEQ ID NO 67
<211> LENGTH: 262
<212> TYPE: PRT
<213> ORGANISM: Homo sapiens

<400> SEQUENCE: 67

Met Lys Phe Leu Ala Leu Ala Leu Thr Ile Leu Leu Ala Ala Ala Thr
1               5                   10                  15

Gln Ala Val Pro Met Gln Ala Asp Ala Pro Ser Gln Leu Glu His Val
                20                  25                  30

Lys Val Ala Met Met Glu Tyr Met Ala Gln Val Lys Glu Thr Gly Gln
            35                  40                  45

Arg Ser Ile Asp Leu Leu Asp Asp Thr Glu Phe Lys Glu Tyr Lys Val
        50                  55                  60

```
Gln Leu Ser Gln Ser Leu Asp Asn Leu Gln Gln Tyr Ala Gln Thr Thr
 65                  70                  75                  80

Ser Gln Ser Leu Ala Pro Tyr Ser Glu Ala Phe Gly Ala Gln Leu Thr
                 85                  90                  95

Asp Ala Ala Ala Val Arg Ala Glu Val Met Lys Asp Val Glu Asp
            100                 105                 110

Val Arg Thr Gln Leu Glu Pro Lys Arg Ala Glu Leu Lys Glu Val Leu
            115                 120                 125

Asp Lys His Ile Asp Glu Tyr Arg Lys Lys Leu Glu Pro Leu Ile Lys
        130                 135                 140

Glu Ile Val Glu Gln Arg Arg Thr Glu Leu Glu Ala Phe Arg Val Lys
145                 150                 155                 160

Met Glu Pro Val Val Glu Glu Met Arg Ala Lys Val Ser Thr Asn Val
                165                 170                 175

Glu Glu Thr Lys Ala Lys Leu Met Pro Ile Val Glu Thr Val Arg Ala
            180                 185                 190

Lys Leu Thr Glu Arg Leu Glu Glu Leu Arg Thr Leu Ala Ala Pro Tyr
        195                 200                 205

Ala Glu Glu Tyr Lys Glu Gln Met Phe Lys Ala Val Gly Glu Val Arg
    210                 215                 220

Glu Lys Val Gly Pro Leu Thr Asn Asp Phe Lys Gly Gln Val Gly Pro
225                 230                 235                 240

Ala Ala Glu Gln Ala Lys Glu Lys Leu Met Asp Phe Tyr Glu Thr Ile
                245                 250                 255

Ser Gln Ala Met Lys Ala
            260

<210> SEQ ID NO 68
<211> LENGTH: 258
<212> TYPE: PRT
<213> ORGANISM: Homo sapiens

<400> SEQUENCE: 68

Met Lys Phe Leu Val Leu Ala Leu Thr Ile Leu Leu Ala Ala Gly Thr
  1               5                  10                  15

Gln Ala Phe Pro Met Gln Ala Asp Ala Pro Ser Gln Leu Glu His Val
                 20                  25                  30

Lys Ala Ala Leu Asn Met Tyr Ile Ala Gln Val Lys Leu Thr Ala Gln
             35                  40                  45

Arg Ser Ile Asp Leu Leu Asp Asp Thr Glu Tyr Lys Glu Tyr Lys Met
 50                  55                  60

Gln Leu Ser Gln Ser Leu Asp Asn Leu Gln Gln Phe Ala Asp Ser Thr
 65                  70                  75                  80

Ser Lys Ser Trp Pro Pro Thr Pro Arg Ser Ser Ala Pro Ser Cys Asp
                 85                  90                  95

Ala Thr Ala Thr Val Arg Ala Glu Val Met Lys Asp Val Glu Asp Val
            100                 105                 110

Arg Thr Gln Leu Glu Pro Lys Arg Ala Glu Leu Thr Glu Val Leu Asn
        115                 120                 125

Lys His Ile Asp Glu Tyr Arg Lys Lys Leu Glu Pro Leu Ile Lys Gln
    130                 135                 140

His Ile Glu Leu Arg Arg Thr Glu Met Asp Ala Phe Arg Ala Lys Ile
145                 150                 155                 160

Asp Pro Val Val Glu Glu Met Arg Ala Lys Val Ala Val Asn Val Glu
```

```
                       165                 170                 175
Glu Thr Lys Thr Lys Leu Met Pro Ile Val Glu Ile Val Arg Ala Lys
                180                 185                 190
Leu Thr Glu Arg Leu Glu Glu Leu Arg Thr Leu Ala Ala Pro Tyr Ala
            195                 200                 205
Glu Glu Tyr Lys Glu Gln Met Phe Lys Ala Val Gly Glu Val Arg Glu
        210                 215                 220
Lys Val Ala Pro Leu Ser Glu Asp Phe Lys Ala Arg Trp Ala Pro Pro
225                 230                 235                 240
Pro Arg Arg Pro Ser Lys Ser Ser Trp Leu Ser Thr Arg Pro Ser Ala
                245                 250                 255
Arg Pro

<210> SEQ ID NO 69
<211> LENGTH: 262
<212> TYPE: PRT
<213> ORGANISM: Homo sapiens

<400> SEQUENCE: 69

Met Lys Phe Val Ala Leu Ala Leu Thr Leu Leu Ala Leu Gly Ser
1               5                   10                  15
Gln Ala Asn Leu Phe Gln Ala Asp Ala Pro Thr Gln Leu Glu His Tyr
                20                  25                  30
Lys Ala Ala Ala Leu Val Tyr Leu Asn Gln Val Lys Asp Gln Ala Glu
            35                  40                  45
Lys Ala Leu Asp Asn Leu Asp Gly Thr Asp Tyr Glu Gln Tyr Lys Leu
        50                  55                  60
Gln Leu Ser Glu Ser Leu Thr Lys Leu Gln Glu Tyr Ala Gln Thr Thr
65                  70                  75                  80
Ser Gln Ala Leu Thr Pro Tyr Ala Glu Thr Ile Ser Thr Gln Leu Met
                85                  90                  95
Glu Asn Thr Lys Gln Leu Arg Glu Arg Val Met Thr Asp Val Glu Asp
                100                 105                 110
Leu Arg Ser Lys Leu Glu Pro His Arg Ala Glu Leu Tyr Thr Ala Leu
            115                 120                 125
Gln Lys His Ile Asp Glu Tyr Arg Glu Lys Leu Glu Pro Val Phe Gln
        130                 135                 140
Glu Tyr Ser Ala Leu Asn Arg Gln Asn Ala Glu Gln Leu Arg Ala Lys
145                 150                 155                 160
Leu Glu Pro Leu Met Asp Asp Ile Arg Lys Ala Phe Glu Ser Asn Ile
                165                 170                 175
Glu Glu Thr Lys Ser Lys Val Val Pro Met Val Glu Ala Val Arg Thr
                180                 185                 190
Lys Leu Thr Glu Arg Leu Glu Asp Leu Arg Thr Met Ala Ala Pro Tyr
            195                 200                 205
Ala Glu Glu Tyr Lys Glu Gln Leu Val Lys Ala Val Glu Glu Ala Arg
        210                 215                 220
Glu Lys Ile Ala Pro His Thr Gln Asp Leu Gln Thr Arg Met Glu Pro
225                 230                 235                 240
Tyr Met Glu Asn Val Arg Thr Thr Phe Ala Gln Met Tyr Glu Thr Ile
                245                 250                 255
Ala Lys Ala Ile Gln Ala
            260
```

```
<210> SEQ ID NO 70
<211> LENGTH: 260
<212> TYPE: PRT
<213> ORGANISM: Homo sapiens

<400> SEQUENCE: 70

Met Lys Phe Ala Ala Leu Ala Leu Ala Leu Leu Ala Val Gly Ser
1               5                   10                  15

His Ala Ala Ser Met Gln Ala Asp Ala Pro Ser Gln Leu Asp His Ala
            20                  25                  30

Arg Ala Val Leu Asp Val Tyr Leu Thr Gln Val Lys Asp Met Ser Leu
        35                  40                  45

Arg Ala Val Asn Gln Leu Asp Asp Pro Gln Tyr Ala Glu Phe Lys Thr
    50                  55                  60

Asn Leu Ala Gln Arg Ile Glu Glu Met Tyr Thr Gln Ile Lys Thr Leu
65                  70                  75                  80

Gln Gly Ser Val Ser Pro Met Thr Asp Ser Phe Tyr Asn Thr Val Met
                85                  90                  95

Glu Val Thr Lys Asp Thr Arg Glu Ser Leu Asn Val Asp Leu Glu Ala
            100                 105                 110

Leu Lys Ser Ser Leu Ala Pro Gln Asn Glu Gln Leu Lys Gln Val Ile
        115                 120                 125

Glu Lys His Leu Asn Asp Tyr Arg Thr Leu Leu Thr Pro Ile Tyr Asn
    130                 135                 140

Asp Tyr Lys Thr Lys His Asp Glu Glu Met Ala Ala Leu Lys Thr Arg
145                 150                 155                 160

Leu Glu Pro Val Met Glu Glu Leu Arg Thr Lys Ile Gln Ala Asn Val
                165                 170                 175

Glu Glu Thr Lys Ala Val Leu Met Pro Met Val Glu Thr Val Arg Thr
            180                 185                 190

Lys Val Thr Glu Arg Leu Glu Ser Leu Arg Glu Val Val Gln Pro Tyr
        195                 200                 205

Val Gln Glu Tyr Lys Glu Gln Met Lys Gln Met Tyr Asp Gln Ala Gln
    210                 215                 220

Thr Val Asp Thr Asp Ala Leu Arg Thr Lys Ile Thr Pro Leu Val Glu
225                 230                 235                 240

Glu Ile Lys Val Lys Met Asn Ala Ile Phe Glu Ile Ile Ala Ala Ser
                245                 250                 255

Val Thr Lys Ser
            260

<210> SEQ ID NO 71
<211> LENGTH: 396
<212> TYPE: PRT
<213> ORGANISM: Homo sapiens

<400> SEQUENCE: 71

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
```

```
              65                  70                  75                  80
Val Pro Phe Ala Thr Glu Leu His Glu Arg Leu Ala Lys Asp Ser Glu
                    85                  90                  95

Lys Leu Lys Glu Glu Ile Gly Lys Glu Leu Glu Glu Leu Arg Ala Arg
                100                 105                 110

Leu Leu Pro His Ala Asn Glu Val Ser Gln Lys Ile Gly Asp Asn Leu
                115                 120                 125

Arg Glu Leu Gln Gln Arg Leu Glu Pro Tyr Ala Asp Gln Leu Arg Thr
            130                 135                 140

Gln Val Asn Thr Gln Ala Glu Gln Leu Arg Arg Gln Leu Thr Pro Tyr
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
                180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
                260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
                340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 72
<211> LENGTH: 429
<212> TYPE: PRT
<213> ORGANISM: Homo sapiens

<400> SEQUENCE: 72

Met Phe Leu Lys Ala Val Val Leu Thr Leu Ala Leu Val Ala Val Thr
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Ala Lys Glu Ala Val Glu His
            35                  40                  45
```

```
Leu Gln Lys Ser Glu Leu Thr Gln Gln Leu Asn Ala Leu Phe Gln Asp
 50                  55                  60
Lys Leu Gly Glu Val Asn Thr Tyr Ala Gly Asp Leu Gln Lys Lys Leu
 65                  70                  75                  80
Val Pro Phe Ala Thr Glu Leu His Glu Arg Leu Ala Lys Asp Ser Glu
                 85                  90                  95
Lys Leu Lys Glu Glu Ile Arg Lys Glu Leu Glu Glu Val Arg Ala Arg
            100                 105                 110
Leu Leu Pro His Ala Asn Glu Val Ser Gln Lys Ile Gly Glu Asn Val
            115                 120                 125
Arg Glu Leu Gln Gln Arg Leu Glu Pro Tyr Thr Asp Gln Leu Arg Thr
130                 135                 140
Gln Val Asn Thr Gln Thr Glu Gln Leu Arg Arg Gln Leu Thr Pro Tyr
145                 150                 155                 160
Ala Gln Arg Met Glu Arg Val Leu Arg Glu Asn Ala Asp Ser Leu Gln
                165                 170                 175
Thr Ser Leu Arg Pro His Ala Asp Gln Leu Lys Ala Lys Ile Asp Gln
            180                 185                 190
Asn Val Glu Glu Leu Lys Glu Arg Leu Thr Pro Tyr Ala Asp Glu Phe
            195                 200                 205
Lys Val Lys Ile Asp Gln Thr Val Glu Glu Leu Arg Arg Ser Leu Ala
210                 215                 220
Pro Tyr Ala Gln Asp Ala Gln Glu Lys Leu Asn His Gln Leu Glu Gly
225                 230                 235                 240
Leu Ala Phe Gln Met Lys Lys Asn Ala Glu Glu Leu Lys Ala Arg Ile
                245                 250                 255
Ser Ala Ser Ala Glu Glu Leu Arg Gln Arg Leu Ala Pro Leu Ala Glu
            260                 265                 270
Asp Met Arg Gly Asn Leu Arg Gly Asn Thr Glu Gly Leu Gln Lys Ser
            275                 280                 285
Leu Ala Glu Leu Gly Gly His Leu Asp Arg His Val Glu Glu Phe Arg
290                 295                 300
Leu Arg Val Glu Pro Tyr Gly Glu Asn Phe Asn Lys Ala Leu Val Gln
305                 310                 315                 320
Gln Met Glu Gln Leu Arg Gln Lys Leu Gly Pro His Ala Gly Asp Val
                325                 330                 335
Glu Gly His Leu Ser Phe Leu Glu Lys Asp Leu Arg Asp Lys Val Asn
            340                 345                 350
Ser Phe Phe Ser Thr Phe Lys Glu Lys Glu Ser Gln Asp Asn Thr Leu
            355                 360                 365
Ser Leu Pro Glu Pro Glu Gln Gln Arg Glu Gln Gln Gln Glu Gln Gln
370                 375                 380
Gln Glu Gln Glu Gln Glu Gln Gln Gln Glu Gln Gln Gln Glu Gln Gln
385                 390                 395                 400
Gln Glu Gln Gln Arg Gln Gln Gln Glu Gln Gln Gln Glu Gln Glu Gln
                405                 410                 415
Gln Gln Glu Gln Val Gln Met Leu Ala Pro Leu Glu Ser
            420                 425

<210> SEQ ID NO 73
<211> LENGTH: 395
<212> TYPE: PRT
<213> ORGANISM: Homo sapiens

<400> SEQUENCE: 73
```

Met Phe Leu Lys Ala Ala Val Leu Thr Leu Ala Leu Val Ala Ile Thr
1               5                   10                  15

Gly Thr Arg Ala Glu Val Thr Ser Asp Gln Val Ala Asn Val Val Trp
            20                  25                  30

Asp Tyr Phe Thr Gln Leu Ser Asn Asn Ala Lys Glu Ala Val Glu Gln
            35                  40                  45

Phe Gln Lys Thr Asp Val Thr Gln Gln Leu Ser Thr Leu Phe Gln Asp
50                  55                  60

Lys Leu Gly Asp Ala Ser Thr Tyr Ala Asp Gly Val His Asn Lys Leu
65                  70                  75                  80

Val Pro Phe Val Val Gln Leu Ser Gly His Leu Ala Lys Glu Thr Glu
                85                  90                  95

Arg Val Lys Glu Glu Ile Lys Lys Leu Glu Asp Leu Arg Asp Arg
                100                 105                 110

Met Met Pro His Ala Asn Lys Val Thr Gln Thr Phe Gly Glu Asn Met
            115                 120                 125

Gln Lys Leu Gln Glu His Leu Lys Pro Tyr Ala Val Asp Leu Gln Asp
            130                 135                 140

Gln Ile Asn Thr Gln Thr Gln Glu Met Lys Leu Gln Leu Thr Pro Tyr
145                 150                 155                 160

Ile Gln Arg Met Gln Thr Thr Ile Lys Glu Asn Val Asp Asn Leu His
                165                 170                 175

Thr Ser Met Met Pro Leu Ala Thr Asn Leu Lys Asp Lys Phe Asn Arg
                180                 185                 190

Asn Met Glu Glu Leu Lys Gly His Leu Thr Pro Arg Ala Asn Glu Leu
            195                 200                 205

Lys Ala Thr Ile Asp Gln Asn Leu Glu Asp Leu Arg Arg Ser Leu Ala
210                 215                 220

Pro Leu Thr Val Gly Val Gln Glu Lys Leu Asn His Gln Met Glu Gly
225                 230                 235                 240

Leu Ala Phe Gln Met Lys Lys Asn Ala Glu Glu Leu Gln Thr Lys Val
                245                 250                 255

Ser Ala Lys Ile Asp Gln Leu Gln Lys Asn Leu Ala Pro Leu Val Glu
                260                 265                 270

Asp Val Gln Ser Lys Val Lys Gly Asn Thr Glu Gly Leu Gln Lys Ser
            275                 280                 285

Leu Glu Asp Leu Asn Arg Gln Leu Glu Gln Gln Val Glu Glu Phe Arg
290                 295                 300

Arg Thr Val Glu Pro Met Gly Glu Met Phe Asn Lys Ala Leu Val Gln
305                 310                 315                 320

Gln Leu Glu Gln Phe Arg Gln Gln Leu Gly Pro Asn Ser Gly Glu Val
                325                 330                 335

Glu Ser His Leu Ser Phe Leu Glu Lys Ser Leu Arg Glu Lys Val Asn
            340                 345                 350

Ser Phe Met Ser Thr Leu Glu Lys Lys Gly Ser Pro Asp Gln Pro Gln
            355                 360                 365

Ala Leu Pro Leu Pro Glu Gln Ala Gln Glu Gln Ala Gln Glu Gln Ala
            370                 375                 380

Gln Glu Gln Val Gln Pro Lys Pro Leu Glu Ser
385                 390                 395

<210> SEQ ID NO 74
<211> LENGTH: 401

```
<212> TYPE: PRT
<213> ORGANISM: Homo sapiens

<400> SEQUENCE: 74

Gly Ala Arg Ala Glu Val Ser Ala Asp Gln Val Ala Thr Val Met Trp
1               5                   10                  15

Asp Tyr Phe Ser Gln Leu Ser Ser Asn Ala Lys Glu Ala Val Glu His
            20                  25                  30

Leu Gln Lys Ser Glu Leu Thr Gln Gln Leu Asn Ala Leu Phe Gln Asp
        35                  40                  45

Lys Leu Gly Glu Val Asn Thr Tyr Ala Gly Asp Leu Gln Lys Lys Leu
    50                  55                  60

Val Pro Phe Ala Thr Glu Leu His Glu Arg Leu Ala Lys Asp Ser Lys
65                  70                  75                  80

Lys Leu Lys Glu Glu Ile Arg Lys Glu Leu Glu Val Arg Ala Arg
                85                  90                  95

Leu Leu Pro His Ala Asn Glu Val Ser Gln Lys Ile Gly Glu Asn Val
            100                 105                 110

Arg Glu Leu Gln Gln Arg Leu Glu Pro Tyr Thr Asp Gln Leu Arg Thr
        115                 120                 125

Gln Val Asn Thr Gln Thr Glu Gln Leu Arg Arg Gln Leu Thr Pro Tyr
    130                 135                 140

Ala Gln Arg Met Glu Arg Val Leu Arg Glu Asn Ala Asp Ser Leu Gln
145                 150                 155                 160

Thr Ser Leu Arg Pro His Ala Asp Gln Leu Lys Ala Lys Ile Asp Gln
                165                 170                 175

Asn Val Glu Glu Leu Lys Gly Arg Leu Thr Pro Tyr Ala Asp Glu Phe
            180                 185                 190

Lys Val Lys Ile Asp Gln Thr Val Glu Glu Leu Arg Arg Ser Leu Ala
        195                 200                 205

Pro Tyr Ala Gln Asp Ala Gln Glu Lys Leu Asn His Gln Leu Glu Gly
    210                 215                 220

Leu Ala Phe Gln Met Lys Lys Asn Ala Glu Glu Leu Lys Ala Arg Ile
225                 230                 235                 240

Ser Ala Ser Ala Glu Glu Leu Arg Gln Arg Leu Ala Pro Leu Ala Glu
                245                 250                 255

Asp Met Arg Gly Asn Leu Arg Gly Asn Thr Glu Gly Leu Gln Lys Ser
            260                 265                 270

Leu Ala Glu Leu Gly Gly His Leu Asp Arg His Val Glu Glu Phe Arg
        275                 280                 285

Leu Arg Val Glu Pro Tyr Gly Glu Asn Phe Asn Lys Ala Leu Val Gln
    290                 295                 300

Gln Met Glu Gln Leu Arg Gln Lys Leu Gly Pro His Ala Gly Asp Val
305                 310                 315                 320

Glu Gly His Leu Ser Phe Leu Glu Lys Asp Leu Arg Asp Lys Val Asn
                325                 330                 335

Ser Phe Phe Ser Thr Phe Lys Glu Lys Glu Ser Gln Asp Asn Thr Leu
            340                 345                 350

Ser Leu Pro Glu Pro Glu Gln Gln Glu Gln Gln Glu Gln Glu Gln Glu
        355                 360                 365

Gln Gln Gln Glu Gln Glu Gln Glu Gln Gln Glu Gln Glu Gln Glu Gln
    370                 375                 380

Glu Gln Glu Gln Gln Glu Gln Val Gln Met Leu Ala Pro Leu Glu
385                 390                 395                 400
```

Ser

<210> SEQ ID NO 75
<211> LENGTH: 382
<212> TYPE: PRT
<213> ORGANISM: Homo sapiens

<400> SEQUENCE: 75

```
Met Phe Leu Lys Ala Val Val Leu Ser Leu Ala Leu Val Ala Val Thr
1               5                   10                  15

Gly Ala Arg Ala Glu Val Asn Ala Asp Gln Val Ala Thr Val Met Trp
            20                  25                  30

Asp Tyr Phe Ser Gln Leu Gly Ser Asn Ala Lys Lys Ala Val Glu His
        35                  40                  45

Leu Gln Lys Ser Glu Leu Thr Gln Gln Leu Asn Thr Leu Phe Gln Asp
    50                  55                  60

Lys Leu Gly Glu Val Asn Thr Tyr Thr Glu Asp Leu Gln Lys Lys Leu
65                  70                  75                  80

Val Pro Phe Ala Thr Glu Leu His Glu Arg Leu Thr Lys Asp Ser Glu
                85                  90                  95

Lys Leu Lys Glu Glu Ile Arg Arg Glu Leu Glu Glu Leu Arg Ala Arg
            100                 105                 110

Leu Leu Pro His Ala Thr Glu Val Ser Gln Lys Ile Gly Asp Asn Val
        115                 120                 125

Arg Glu Leu Gln Gln Arg Leu Gly Pro Phe Thr Gly Gly Leu Arg Thr
    130                 135                 140

Gln Val Asn Thr Gln Val Gln Leu Gln Arg Gln Leu Lys Pro Tyr
145                 150                 155                 160

Ala Glu Arg Met Glu Ser Val Leu Arg Gln Asn Ile Arg Asn Leu Glu
                165                 170                 175

Ala Ser Val Ala Pro Tyr Ala Asp Glu Phe Lys Ala Lys Ile Asp Gln
            180                 185                 190

Asn Val Glu Glu Leu Lys Gly Ser Leu Thr Pro Tyr Ala Glu Glu Leu
        195                 200                 205

Lys Ala Lys Ile Asp Gln Asn Val Glu Glu Leu Arg Arg Ser Leu Ala
    210                 215                 220

Pro Tyr Ala Gln Asp Val Gln Glu Lys Leu Asn His Gln Leu Glu Gly
225                 230                 235                 240

Leu Ala Phe Gln Met Lys Lys Gln Ala Glu Glu Leu Lys Ala Lys Ile
                245                 250                 255

Ser Ala Asn Ala Asp Glu Leu Arg Gln Lys Leu Val Pro Val Ala Glu
            260                 265                 270

Asn Val His Gly His Leu Lys Gly Asn Thr Glu Gly Leu Gln Lys Ser
        275                 280                 285

Leu Leu Glu Leu Arg Ser His Leu Asp Gln Gln Val Glu Glu Phe Arg
    290                 295                 300

Leu Lys Val Glu Pro Tyr Gly Glu Thr Phe Asn Lys Ala Leu Val Gln
305                 310                 315                 320

Gln Val Glu Asp Leu Arg Gln Lys Leu Gly Pro Leu Ala Gly Asp Val
                325                 330                 335

Glu Gly His Leu Ser Phe Leu Glu Lys Asp Leu Arg Asp Lys Val Asn
            340                 345                 350

Thr Phe Phe Ser Thr Leu Lys Glu Glu Ala Ser Gln Gly Gln Ser Gln
        355                 360                 365
```

Ala Leu Pro Ala Gln Glu Lys Ala Gln Ala Pro Leu Glu Gly
370             375             380

<210> SEQ ID NO 76
<211> LENGTH: 391
<212> TYPE: PRT
<213> ORGANISM: Homo sapiens

<400> SEQUENCE: 76

Met Phe Leu Lys Ala Val Val Leu Thr Val Ala Leu Val Ala Ile Thr
1               5                   10                  15

Gly Thr Gln Ala Glu Val Thr Ser Asp Gln Val Ala Asn Val Met Trp
            20                  25                  30

Asp Tyr Phe Thr Gln Leu Ser Asn Asn Ala Lys Glu Ala Val Glu Gln
        35                  40                  45

Leu Gln Lys Thr Asp Val Thr Gln Gln Leu Asn Thr Leu Phe Gln Asp
    50                  55                  60

Lys Leu Gly Asn Ile Asn Thr Tyr Ala Asp Asp Leu Gln Asn Lys Leu
65                  70                  75                  80

Val Pro Phe Ala Val Gln Leu Ser Gly His Leu Thr Lys Glu Thr Glu
                85                  90                  95

Arg Val Arg Glu Glu Ile Gln Lys Glu Leu Glu Asp Leu Arg Ala Asn
            100                 105                 110

Met Met Pro His Ala Asn Lys Val Ser Gln Met Phe Gly Asp Asn Val
        115                 120                 125

Gln Lys Leu Gln Glu His Leu Arg Pro Tyr Ala Thr Asp Leu Gln Ala
    130                 135                 140

Gln Ile Asn Ala Gln Thr Gln Asp Met Lys Arg Gln Leu Thr Pro Tyr
145                 150                 155                 160

Ile Gln Arg Met Gln Thr Thr Ile Gln Asp Asn Val Glu Asn Leu Gln
                165                 170                 175

Ser Ser Met Val Pro Phe Ala Asn Glu Leu Lys Glu Lys Phe Asn Gln
            180                 185                 190

Asn Met Glu Gly Leu Lys Gly Gln Leu Thr Pro Arg Ala Asn Glu Leu
        195                 200                 205

Lys Ala Thr Ile Asp Gln Asn Leu Glu Asp Leu Arg Ser Arg Leu Ala
    210                 215                 220

Pro Leu Ala Glu Gly Val Gln Glu Lys Leu Asn His Gln Met Glu Gly
225                 230                 235                 240

Leu Ala Phe Gln Met Lys Lys Asn Ala Glu Glu Leu Gln Thr Lys Val
                245                 250                 255

Ser Thr Asn Ile Asp Gln Leu Gln Lys Asn Leu Ala Pro Leu Val Glu
            260                 265                 270

Asp Val Gln Ser Lys Leu Lys Gly Asn Thr Glu Gly Leu Gln Lys Ser
        275                 280                 285

Leu Glu Asp Leu Asn Lys Gln Leu Asp Gln Gln Val Glu Val Phe Arg
    290                 295                 300

Arg Ala Val Glu Pro Leu Gly Asp Lys Phe Asn Met Ala Leu Val Gln
305                 310                 315                 320

Gln Met Glu Lys Phe Arg Gln Gln Leu Gly Ser Asp Ser Gly Asp Val
                325                 330                 335

Glu Ser His Leu Ser Phe Leu Glu Lys Asn Leu Arg Glu Lys Val Ser
            340                 345                 350

Ser Phe Met Ser Thr Leu Gln Lys Lys Gly Ser Pro Asp Gln Pro Leu

```
                355                 360                 365
Ala Leu Pro Leu Pro Glu Gln Val Gln Glu Gln Val Gln Glu Gln Val
            370                 375                 380

Gln Pro Lys Pro Leu Glu Ser
385                 390

<210> SEQ ID NO 77
<211> LENGTH: 285
<212> TYPE: PRT
<213> ORGANISM: Artificial Sequence
<220> FEATURE:
<223> OTHER INFORMATION: Description of Artificial Sequence: Synthetic
      Tetranectin-apolipoprotein A-I

<400> SEQUENCE: 77

Lys Lys Ile Val Asn Ala Lys Lys Asp Val Val Asn Thr Lys Met Phe
1               5                   10                  15

Glu Glu Leu Lys Ser Arg Leu Asp Thr Leu Ala Gln Glu Val Ala Leu
            20                  25                  30

Leu Lys Glu Gln Gln Ala Leu Gln Thr Val Asp Glu Pro Pro Gln Ser
        35                  40                  45

Pro Trp Asp Arg Val Lys Asp Leu Ala Thr Val Tyr Val Asp Val Leu
    50                  55                  60

Lys Asp Ser Gly Arg Asp Tyr Val Ser Gln Phe Glu Gly Ser Ala Leu
65                  70                  75                  80

Gly Lys Gln Leu Asn Leu Lys Leu Leu Asp Asn Trp Asp Ser Val Thr
                85                  90                  95

Ser Thr Phe Ser Lys Leu Arg Glu Gln Leu Gly Pro Val Thr Gln Glu
            100                 105                 110

Phe Trp Asp Asn Leu Glu Lys Glu Thr Glu Gly Leu Arg Gln Glu Met
        115                 120                 125

Ser Lys Asp Leu Glu Glu Val Lys Ala Lys Val Gln Pro Tyr Leu Asp
    130                 135                 140

Asp Phe Gln Lys Lys Trp Gln Glu Glu Met Glu Leu Tyr Arg Gln Lys
145                 150                 155                 160

Val Glu Pro Leu Arg Ala Glu Leu Gln Glu Gly Ala Arg Gln Lys Leu
                165                 170                 175

His Glu Leu Gln Glu Lys Leu Ser Pro Leu Gly Glu Glu Met Arg Asp
            180                 185                 190

Arg Ala Arg Ala His Val Asp Ala Leu Arg Thr His Leu Ala Pro Tyr
        195                 200                 205

Ser Asp Glu Leu Arg Gln Arg Leu Ala Ala Arg Leu Glu Ala Leu Lys
    210                 215                 220

Glu Asn Gly Gly Ala Arg Leu Ala Glu Tyr His Ala Lys Ala Thr Glu
225                 230                 235                 240

His Leu Ser Thr Leu Ser Glu Lys Ala Lys Pro Ala Leu Glu Asp Leu
                245                 250                 255

Arg Gln Gly Leu Leu Pro Val Leu Glu Ser Phe Lys Val Ser Phe Leu
            260                 265                 270

Ser Ala Leu Glu Glu Tyr Thr Lys Lys Leu Asn Thr Gln
        275                 280                 285

<210> SEQ ID NO 78
<211> LENGTH: 288
<212> TYPE: PRT
<213> ORGANISM: Artificial Sequence
<220> FEATURE:
```

<223> OTHER INFORMATION: Description of Artificial Sequence: Synthetic
      Tetrancetin Apolipoprotein A-I

<400> SEQUENCE: 78

```
Ile Val Asn Ala Lys Lys Asp Val Val Asn Thr Lys Met Phe Glu Glu
1               5                   10                  15

Leu Lys Ser Arg Leu Asp Thr Leu Ala Gln Glu Val Ala Leu Leu Lys
            20                  25                  30

Glu Gln Gln Ala Leu Gln Thr Val Ser Leu Lys Gly Thr Asp Glu Pro
        35                  40                  45

Pro Gln Ser Pro Trp Asp Arg Val Lys Asp Leu Ala Thr Val Tyr Val
    50                  55                  60

Asp Val Leu Lys Asp Ser Gly Arg Asp Tyr Val Ser Gln Phe Glu Gly
65                  70                  75                  80

Ser Ala Leu Gly Lys Gln Leu Asn Leu Lys Leu Leu Asp Asn Trp Asp
                85                  90                  95

Ser Val Thr Ser Thr Phe Ser Lys Leu Arg Glu Gln Leu Gly Pro Val
            100                 105                 110

Thr Gln Glu Phe Trp Asp Asn Leu Glu Lys Glu Thr Glu Gly Leu Arg
        115                 120                 125

Gln Glu Met Ser Lys Asp Leu Glu Glu Val Lys Ala Lys Val Gln Pro
    130                 135                 140

Tyr Leu Asp Asp Phe Gln Lys Lys Trp Gln Glu Glu Met Glu Leu Tyr
145                 150                 155                 160

Arg Gln Lys Val Glu Pro Leu Arg Ala Glu Leu Gln Glu Gly Ala Arg
                165                 170                 175

Gln Lys Leu His Glu Leu Gln Glu Lys Leu Ser Pro Leu Gly Glu Glu
            180                 185                 190

Met Arg Asp Arg Ala Arg Ala His Val Asp Ala Leu Arg Thr His Leu
        195                 200                 205

Ala Pro Tyr Ser Asp Glu Leu Arg Gln Arg Leu Ala Ala Arg Leu Glu
    210                 215                 220

Ala Leu Lys Glu Asn Gly Gly Ala Arg Leu Ala Glu Tyr His Ala Lys
225                 230                 235                 240

Ala Thr Glu His Leu Ser Thr Leu Ser Glu Lys Ala Lys Pro Ala Leu
                245                 250                 255

Glu Asp Leu Arg Gln Gly Leu Leu Pro Val Leu Glu Ser Phe Lys Val
            260                 265                 270

Ser Phe Leu Ser Ala Leu Glu Glu Tyr Thr Lys Lys Leu Asn Thr Gln
        275                 280                 285
```

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
      pro-polypeptide 5803

<400> SEQUENCE: 79

```
Met Arg Gly Ser His His His His His His Gly Ser Pro Arg Pro Pro
1               5                   10                  15

Thr Pro
```

<210> SEQ ID NO 80
<211> LENGTH: 27
<212> TYPE: PRT

<213> ORGANISM: Artificial Sequence
<220> FEATURE:
<223> OTHER INFORMATION: Description of Artificial Sequence: Synthetic plasmid 5816

<400> SEQUENCE: 80

Met Cys Asp Leu Pro Gln Thr His Ser Leu Gly Ser His His His
1               5                   10                  15

His His Gly Ser Val Val Ala Pro Pro Ala Pro
            20                  25

<210> SEQ ID NO 81
<211> LENGTH: 146
<212> TYPE: PRT
<213> ORGANISM: Artificial Sequence
<220> FEATURE:
<223> OTHER INFORMATION: Description of Artificial Sequence: Synthetic plasmid 5820

<400> SEQUENCE: 81

Met Arg Gly Ser His His His His His His Gly Ser Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Val Val Ala Pro Pro
    130                 135                 140

Ala Pro
145

<210> SEQ ID NO 82
<211> LENGTH: 23
<212> TYPE: PRT
<213> ORGANISM: Artificial Sequence
<220> FEATURE:
<223> OTHER INFORMATION: Description of Artificial Sequence: Synthetic plasmid 5805

<400> SEQUENCE: 82

Met Arg Gly Ser His His His His His His Ala His Phe Trp Gln Gln
1               5                   10                  15

Ala Pro Arg Pro Pro Thr Pro
            20

<210> SEQ ID NO 83
<211> LENGTH: 139
<212> TYPE: PRT
<213> ORGANISM: Artificial Sequence
<220> FEATURE:
<223> OTHER INFORMATION: Description of Artificial Sequence: Synthetic plasmid 5819

-continued

<400> SEQUENCE: 83

```
Met Arg Gly Ser His His His His His His Thr Asp Pro Glu Phe Gln
1               5                   10                  15

Gln Gln Gln Gln Leu Leu Asp Val Val Lys Arg Gln Gln Glu Leu Leu
            20                  25                  30

Arg Leu Thr Val Trp Gly Thr Lys Asn Leu Gln Ala Arg Val Thr Ala
        35                  40                  45

Ile Glu Lys Tyr Leu Gln Asp Gln Ala Arg Leu Asn Ser Trp Gly Cys
    50                  55                  60

Ala Phe Arg Gln Val Cys His Thr Thr Val Pro Trp Val Asn Asp Ser
65                  70                  75                  80

Leu Ala Pro Asp Trp Asp Asn Met Thr Trp Gln Glu Trp Glu Lys Gln
                85                  90                  95

Val Arg Tyr Leu Glu Ala Asn Ile Ser Lys Ser Leu Glu Gln Ala Gln
            100                 105                 110

Ile Gln Gln Glu Lys Asn Met Tyr Glu Leu Gln Lys Leu Asn Ser Trp
        115                 120                 125

Asp Ile Arg Ser Val Val Ala Pro Pro Ala Pro
    130                 135
```

<210> SEQ ID NO 84
<211> LENGTH: 21
<212> TYPE: PRT
<213> ORGANISM: Artificial Sequence
<220> FEATURE:
<223> OTHER INFORMATION: Description of Artificial Sequence: Synthetic
      plasmid 5806

<400> SEQUENCE: 84

```
Met His His His His His His Lys Ala Lys Arg Phe Lys Lys His Pro
1               5                   10                  15

Arg Pro Pro Ala Pro
            20
```

<210> SEQ ID NO 85
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

```
Met Arg Gly Ser His His His His His His Thr Asp Pro Glu Phe Gln
1               5                   10                  15

Gln Gln Gln Gln Leu Leu Asp Val Val Lys Arg Gln Gln Glu Leu Leu
            20                  25                  30

Arg Leu Thr Val Trp Gly Thr Lys Asn Leu Gln Ala Arg Val Thr Ala
        35                  40                  45

Ile Glu Lys Tyr Leu Gln Asp Gln Ala Arg Leu Asn Ser Trp Gly Cys
    50                  55                  60

Ala Phe Arg Gln Val Cys His Thr Thr Val Pro Trp Val Asn Asp Ser
65                  70                  75                  80

Leu Ala Pro Asp Trp Asp Asn Met Thr Trp Gln Glu Trp Glu Lys Gln
                85                  90                  95

Val Arg Tyr Leu Glu Ala Asn Ile Ser Lys Ser Leu Glu Gln Ala Gln
            100                 105                 110
```

-continued

```
Ile Gln Gln Glu Lys Asn Met Tyr Glu Leu Gln Lys Leu Asn Ser Trp
        115                 120                 125

Asp Ile Arg Ser Val Val Ala Pro Pro Ala Ala Pro
        130                 135                 140
```

PROKARYOTIC EXPRESSION CONSTRUCT

CROSS-REFERENCE TO RELATED APPLICATIONS

This Application claims priority under 35 U.S.C. §119 to European Application No. EP 10008996.0 filed Aug. 30, 2010, and European Application No. EP 10187663.9 filed Oct. 15, 2010, the disclosures of which are incorporated herein by reference.

SEQUENCE LISTING

The instant application contains a Sequence Listing which has been submitted in ASCII format via EFS-Web and is hereby incorporated by reference in its entirety. Said ASCII copy, created on Apr. 18, 2012, is named P4518.txt and is 111,087 bytes in size.

FIELD OF THE INVENTION

Herein is reported an expression construct for the production of a polypeptide in a prokaryotic cell. The expression construct comprises a pro-polypeptide comprising in N- to C-terminal direction the dipeptide GS, an amino acid tag, the dipeptide GS, and a protease cleavage site.

BACKGROUND OF THE INVENTION

Expression systems for the production of recombinant polypeptides are well-known in the state of the art and are described by, e.g., Marino, M. H., Biopharm. 2 (1989) 18-33; Goeddel, D. V., et al., Methods Enzymol. 185 (1990) 3-7; Wurm, F., and Bernard, A., Curr. Opin. Biotechnol. 10 (1999) 156-159.

Polypeptides, such as antibodies and antibody fusions, for use in pharmaceutical applications are generally produced in mammalian cells such as CHO cells, NS0 cells, SP2/0 cells, COS cells, HEK cells, BHK cells, PER.C6™ cells, or the like. The elements of an eukaryotic expression plasmid are generally a prokaryotic plasmid propagation unit, for example for E. coli, comprising a prokaryotic origin of replication and a prokaryotic selection marker, an eukaryotic selection marker, and one or more expression cassettes for the expression of the structural gene(s) of interest each comprising a promoter, a structural gene, and a transcription terminator including a polyadenylation signal. For transient expression in mammalian cells a mammalian origin of replication, such as the SV40 Ori or OriP, can be included. As promoter a constitutive or inducible promoter can be selected. For optimized transcription a Kozak sequence may be included in the 5' untranslated region. For mRNA processing, in particular mRNA splicing and transcription termination, mRNA splicing signals, depending on the organization of the structural gene (exon/intron organization), may be included as well as a polyadenylation signal.

Other polypeptides for use in pharmaceutical applications, e.g. insulin, interferon alpha-2, somatotropin, interleukin-2, GM-CSF and Reteplase, can be produced in prokaryotic cells, yeast, and mainly E. coli. The elements of an E. coli expression plasmid are generally an origin of replication, a selection marker, and one or more expression cassettes for the expression of the structural gene(s) of interest. An expression cassette generally comprises a promoter, a structural gene, and a transcription terminator. As promoter a constitutive or inducible promoter can be used. For optimized transcription a Shine-Dalgarno-Sequence or a variant thereof preceding the start codon of mRNA may be included in the 5' untranslated region.

SUMMARY OF THE INVENTION

Herein is reported a pro-polypeptide which is useful for the expression of a polypeptide of interest in a prokaryotic cell. Therefore the pro-polypeptide is fused to the N-terminus of the polypeptide of interest. The pro-polypeptide as reported herein provides for improved expression yields and improves the handling of the fusion polypeptide (downstream processing, purification). For example, efficient endotoxin removal is effected while the protein of interest comprising the pro-polypeptide is bound e.g. to an affinity chromatography material. Thereafter the pro-polypeptide can efficiently be cleaved from the polypeptide of interest by the incorporated protease cleavage site with the cognate protease.

Herein is reported as one aspect a pro-polypeptide comprising in N- to C-terminal direction
  a first dipeptide with the amino acid sequence GS,
  an amino acid sequence tag,
  a second dipeptide with the amino acid sequence GS immediately adjacent to
  an enzymatic cleavage site.

In one embodiment the pro-polypeptide comprises a leading amino acid sequence N-terminal to the first dipeptide with the amino acid sequence GS. In another embodiment the leading amino acid sequence has a length of at least two amino acid residues and at most of twenty amino acid residues. In a further embodiment the leading amino acid sequence has a length of at least two amino acid residues and at most of ten amino acid residues. In also an embodiment the leading amino acid sequence is a polypeptide with an amino acid sequence selected from SEQ ID NO: 1-8. In a further embodiment the leading amino acid sequence is a polypeptide with an amino acid sequence selected from SEQ ID NO: 1-6.

In one embodiment the pro-polypeptide is consisting in N- to C-terminal direction of
  a leading amino acid sequence,
  a first dipeptide with the amino acid sequence GS,
  an amino acid sequence tag,
  a second dipeptide with the amino acid sequence GS immediately adjacent to
  an enzymatic cleavage site.

A further aspect as reported herein is a fusion polypeptide comprising in N- to C-terminal direction
  optionally a leading amino acid sequence,
  a first dipeptide with the amino acid sequence GS,
  an amino acid sequence tag,
  a second dipeptide with the amino acid sequence GS immediately adjacent to
  an enzymatic cleavage site, and
  a protein of interest.

In one embodiment of all aspect as reported before the amino acid sequence tag has the amino acid sequence selected from SEQ ID NO: 9 to SEQ ID NO: 27. In one embodiment the amino acid sequence tag has the amino acid sequence of SEQ ID NO: 11 or SEQ ID NO: 15. In another embodiment the enzymatic cleavage site has the amino acid sequence selected from SEQ ID NO: 28 to 42. In a further embodiment the polypeptide of interest is selected from antibody heavy or light chain, antibody fragment, single-chain antibody, apolipoprotein, apolipoprotein variant, apolipoprotein fusion, interferon, interleukin, insulin, tissue type plasminogen activator variant, colony-stimulating factor, growth hormone, bone morphogenetic protein. In one embodiment the polypeptide of interest has the amino acid sequence of SEQ ID NO: 43 or SEQ ID NO: 44 or SEQ ID NO: 45. In one embodiment the polypeptide of interest is a polypeptide different from the pro-polypeptide as reported herein, i.e. the polypeptide of interest does not comprise an amino acid sequence corresponding to a dipeptide with the amino acid sequence GS directly fused to an amino acid sequence tag. In one embodiment the amino acid at the N-terminus of the polypeptide of interest has a free alpha-amino group after downstream processing. In one embodiment the pro-polypeptide and/or the polypeptide of interest is not glycosylated.

Herein is reported as another aspect a method for producing a polypeptide of interest comprising the following steps
a) providing a cell comprising a nucleic acid encoding a fusion polypeptide comprising in N- to C-terminal direction
optionally a leading amino acid sequence,
a first dipeptide GS,
an amino acid sequence tag,
a second dipeptide GS immediately adjacent to
an enzymatic cleavage site, and
a polypeptide of interest,
b) cultivating the cell,
c) recovering the fusion polypeptide from the cell or the cultivation medium,
d) purifying the fusion polypeptide,
e) enzymatically cleaving the fusion polypeptide and thereby producing the polypeptide of interest.

In one embodiment the cell is a prokaryotic cell. In another embodiment the cell is an *E. coli* cell or a *Bacillus subtilis* cell. In one embodiment the amino acid sequence tag has the amino acid sequence selected from SEQ ID NO: 9 to SEQ ID NO: 27. In one embodiment the amino acid sequence tag has the amino acid sequence of SEQ ID NO: 11 or SEQ ID NO: 15. In another embodiment the enzymatic cleavage site has the amino acid sequence selected from SEQ ID NO: 28 to 42. In also an embodiment the further polypeptide is selected from antibody heavy or light chains, antibody fragment, single-chain antibody, apolipoprotein, apolipoprotein variant, apolipoprotein fusion, interferon, interleukin, insulin, tissue type plasminogen activator variant, colony-stimulating factor, growth hormone, bone morphogenetic protein. In one embodiment the polypeptide of interest has the amino acid sequence of SEQ ID NO: 43 or SEQ ID NO: 44 or SEQ ID NO: 45. In one embodiment the polypeptide of interest is a polypeptide different from the pro-polypeptide as reported herein, i.e. the further polypeptide does not comprise the dipeptide with the amino acid sequence GS directly fused to an amino acid sequence tag.

Herein is reported as a further aspect a kit of parts comprising a nucleic acid comprising in 5'- to 3'-direction
a nucleic acid encoding the dipeptide with the amino acid sequence GS,
a nucleic acid encoding an amino acid sequence tag,
a nucleic acid encoding the dipeptide with the amino acid sequence GS immediately adjacent to
a nucleic acid encoding an enzymatic cleavage site.

One aspect as reported herein is a method for the cultivation of prokaryotic cells, characterized in that
the cells are cultivated in a medium comprising glucose, yeast extract, L-leucine, L-proline, L-methionine, Thiamin-HCl, anti foam agent,
the cells are fed with a first feed solution comprising yeast extract, glycerol, L-methionine, L-leucine and L-proline,
the cells are fed with a second feed solution comprising L-Proline,
a potassium hydroxide solution and a glucose solution are used for pH control.

One aspect as reported herein is a method for the production of a polypeptide, characterized in that
cells comprising a nucleic acid encoding the polypeptide are cultivated in a medium comprising glucose, yeast extract, L-leucine, L-proline, L-methionine, Thiamin-HCl, anti foam agent,
the cells are fed first with a feed solution comprising yeast extract, glycerol, L-methionine, L-leucine and L-proline,
the cells are fed second with a feed solution comprising L-Proline,
a potassium hydroxide solution and a glucose solution are used for pH control,
wherein the polypeptide is recovered from the cells or from the cultivation medium and thereby a polypeptide is produced.

In one embodiment of the methods as reported herein the addition of the first feed is started at an optical density of about 15 determined at 578 nm, the addition of the second feed is started at an optical density of about 50 determined at 578 nm, and the expression of the polypeptide is induced with IPTG at an optical density of about 90 determined at 578 nm.

In one embodiment of the methods as reported herein the medium comprises about 8.85 g/l glucose, about 63.5 g/l yeast extract, about 2.2 g/l NH$_4$Cl, about 1.95 g/l L-leucine, about 2.9 g/l L-proline, about 0.75 g/l L-methionine, about 17.3 g/l KH$_2$PO$_4$*3H$_2$O, about 2 g/l MgSO$_4$*7H$_2$O, about 25.8 mg/l Thiamin-HCl, about 1.0 ml/l 10% anti foam agent.

In one embodiment of the methods as reported herein the first feed solution comprises about 333 g/l yeast extract, about 333 g/l 85%-glycerol, about 1.7 g/l L-methionine, and about 5 g/l L-leucine and L-proline each.

In one embodiment of the methods as reported herein the second feed solution comprises about 600 g/l L-proline.

In one embodiment of the methods as reported herein the base for pH regulation is a 10% (w/v) KOH solution and the acid is a 75% glucose solution.

In one embodiment of the methods as reported herein the cultivation is at about 25° C.

In one embodiment of the methods as reported herein the cultivation is at a pH between about pH 6.5 and about pH 6.9.

In one embodiment the cultivation is in a volume of about 10 l.

In one embodiment of the methods as reported herein the first feed is started at a rate of 70 g/h.

In one embodiment of the methods as reported herein the second feed is started at a rate of 10 ml/h.

In one embodiment of the methods as reported herein the dissolved oxygen value is kept above 50%. In a specific embodiment the dissolved oxygen value is kept above 50% by increasing stirrer speed, aeration rate, and air pressure in parallel.

In one embodiment of the methods as reported herein the stirrer speed is from about 500 rpm to about 1500 rpm.

In one embodiment of the methods as reported herein the aeration rate is from about 10 l/min to about 20 l/min.

In one embodiment of the methods as reported herein the air pressure is from about 300 mbar to about 500 mbar.

In one embodiment of the methods as reported herein the prokaryotic cell is an *E. coli* cell.

In one embodiment of the methods as reported herein the polypeptide is apolipoprotein A1. In a specific embodiment the apolipoprotein A1 is tetranectin-apolipoprotein A1 precursor protein.

One aspect as reported herein is a cultivation medium for prokaryotic cells comprising about 8.85 g/l glucose, about 63.5 g/l yeast extract, about 2.2 g/l NH$_4$Cl, about 1.95 g/l L-leucine, about 2.9 g/l L-proline, about 0.75 g/l L-methionine, about 17.3 g/l KH$_2$PO$_4$*3H$_2$O, about 2 g/l MgSO$_4$*7H$_2$O, about 25.8 mg/l Thiamin-HCl, about 1.0 ml/l 10% anti foam agent.

In one embodiment the medium further comprises a first feed comprising about 333 g/l yeast extract, about 333 g/l 85%-glycerol, about 1.7 g/l L-methionine, and about 5 g/l L-leucine and L-proline each.

In one embodiment the medium further comprises a second feed solution comprising about 600 g/l L-proline.

DESCRIPTION OF THE SEQUENCE LISTINGS

SEQ ID NO: 1 to 8 amino acid sequences
SEQ ID NO: 9 to 27 amino acid tags
SEQ ID NO: 28 to 42 protease cleavage sites
SEQ ID NO: 43 to 76 apolipoprotein amino acid sequences
SEQ ID NO: 77 to 78 variant apolipoprotein fusion amino acid sequences
SEQ ID NO: 79 to 84 pro-polypeptide amino acid sequence

DETAILED DESCRIPTION OF THE INVENTION

The herein reported pro-polypeptide is useful for the expression of a polypeptide of interest in a prokaryotic cell. It provides for improved expression yields and improves the handling e.g. during downstream processing and purification. For example, efficient endotoxin removal is effected while the protein of interest comprising the pro-polypeptide is bound e.g. to an affinity chromatography material. Thereafter the pro-polypeptide can efficiently be cleaved from the polypeptide of interest by the incorporated protease cleavage site with the cognate protease.

Herein is reported a pro-polypeptide comprising in N- to C-terminal direction
optionally a leading amino acid sequence,
a first dipeptide GS,
an amino acid sequence tag,
a second dipeptide GS immediately adjacent to
an enzymatic cleavage site.

The term "amino acid" or "amino acid residue" as used within this application denotes the group of carboxy α-amino acids, which directly or in form of a precursor can be encoded by a nucleic acid. The individual amino acids are encoded by nucleic acids consisting of three nucleotides, so called codons or base-triplets. Each amino acid is encoded by at least one codon. This is known as "degeneration of the genetic code". The term "amino acid" as used within this application denotes the naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The term "polypeptide" denotes a polymer consisting of amino acids joined by peptide bonds, whether produced naturally or synthetically. Polypeptides of less than about 20 amino acid residues may be referred to as "peptides", whereas molecules consisting of two or more polypeptides or comprising one polypeptide of more than 100 amino acid residues may be referred to as "proteins". The term "dipeptide" denotes a peptide consisting of two amino acid residues connected to each other with a peptide bond. A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless. In one embodiment the polypeptide of interest is an apolipoprotein or an apolipoprotein variant/fusion. In another embodiment the apolipoprotein is an apolipoprotein A1 or an apolipoprotein A1 variant/fusion. In a further embodiment the apolipoprotein A1 is fused N-terminally to a tetranectin trimerization domain resulting in an artificial tetranectin-apolipoprotein A1 fusion polypeptide. In one embodiment the polypeptide of interest has an amino acid sequence selected from SEQ ID NO: 43 to SEQ ID NO: 76. In another embodiment the polypeptide of interest has an amino acid sequence selected from SEQ ID NO: 43, or SEQ ID NO: 44, or SEQ ID NO: 45.

The term "leading amino acid sequence" denotes a sequence of amino acids or amino acid residues connected to each other via peptide bonds. In one embodiment the leading amino acid sequence consists of from one to twenty amino acid residues. In another embodiment the leading amino acid sequence consists of from two to fifteen amino acid residues. In a further embodiment the leading amino acid sequence consists of from four to ten amino acid residues. In also an embodiment the leading amino acid sequence has the amino acid sequence of MR, or SEQ ID NO: 1 (KAKRFKKH), or SEQ ID NO: 2 (AHFWQQA), or SEQ ID NO: 3 (CDLPQTHSL), or SEQ ID NO: 4 (IEPD), or SEQ ID NO: 5 (IEPDSPGT), or SEQ ID NO: 6 (MCDLPQTHSL), or SEQ ID NO: 7 (AEAGITGTWYNQLGSTFIVTAGADGALT-GTYESAVGNAESRYVLTGRYDSAPA-TDGSGTALGWTVAWKNNYRNAHSATTWS-GQYVGGAEARINTQWLLTSGTTEANAWKSTLVGH-DTFTKVKPSAAS), or SEQ ID NO: 8 (TDPEFQQQQQL LDVVKRQQELLRLTVWGTKNLQARVTAIEKYLQD-QARLNSWGCAFRQVCHTTVPWVNDSLAP-DWDNMTWQEWEKQVRYLEANISKSLEQA-QIQQEKNMYELQKLNSWDIRSVV). In a further embodiment the leading amino acid sequence has the amino acid sequence selected from MR, or SEQ ID NO: 1 (KAKRFKKH), or SEQ ID NO: 2 (AHFWQQA), or SEQ ID NO: 3 (CDLPQTHSL), or SEQ ID NO: 4 (IEPD), or SEQ ID NO: 5 (IEPDSPGT), or SEQ ID NO: 6 (MCDLPQTHSL).

The term "amino acid sequence tag" denotes a sequence of amino acid residues connected to each other via peptide bonds that has specific binding properties. In one embodiment the amino acid sequence tag is an affinity or purification tag. In an embodiment the amino acid sequence tag is selected from Arg-tag, His-tag, Flag-tag, 3× Flag-tag, Strep-tag, Nano-tag, SBP-tag, c-myc-tag, S-tag, calmodulin-binding-peptide, cellulose-binding-domain, chitin-binding-domain, GST-tag, or MBP-tag. In a further embodiment the amino acid sequence tag is selected from SEQ ID NO: 9 (RRRRR) or SEQ ID NO: 10 (RRRRRR), or SEQ ID NO: 11 (HHH-HHH), or SEQ ID NO: 12 (KDHLIHNVHKEFHAHAHNK) or SEQ ID NO: 13 (DYKDDDDK) or SEQ ID NO: 14 (DYKDHDGDYKDHDIDYKDDDDK) or SEQ ID NO: 15 (AWRHPQFGG) or SEQ ID NO: 16 (WSHPQFEK) or SEQ ID NO: 17 (MDVEAWLGAR) or SEQ ID NO: 18 (MD-VEAWLGARVPLVET) or SEQ ID NO: 19 (MDEKTTG-WRGGHVVEGLAGELEQLRARLEHHPQGQREP) or SEQ ID NO: 20 (EQKLISEEDL) or SEQ ID NO: 21 (KETAAAKFERQHMDS) or SEQ ID NO: 22 (KRRWKKNFIAVSAANRFKKISSSGAL) or SEQ ID NO: 23 (cellulose binding domain) or SEQ ID NO: 24 (cellulose binding domain) or SEQ ID NO: 25 (TNPGVSAWQVNTAY-TAGQLVTYNGKTYKCLQPHTSLAG-WEPSNVPALWQLQ) or SEQ ID NO: 26 (GST-tag) or SEQ ID NO: 27 (MBP-tag).

The term "enzymatic cleavage site" denotes a sequence of amino acid residues connected to each other via peptides bonds that can specifically be cleaved by a protease. In one embodiment the protease is IgA-protease, Granzyme B, Tev protease, Prescission protease, Thrombin, Factor Xa, or Enterokinase.

The term "IgA-protease" denotes a protease derived from Neisseria gonorrhoeae with a recognition site comprising one of the following sequences wherein "↓" denotes the position of the cleaved bond:

```
                                         (SEQ ID NO: 28)
        Pro-Ala-Pro ↓ Ser-Pro, (SEQ ID NO: 29)
        Pro-Pro ↓ Ser-Pro, (SEQ ID NO: 30)
        Pro-Pro ↓ Ala-Pro, (SEQ ID NO: 31)
        Pro-Pro ↓ Thr-Pro, (SEQ ID NO: 32)
        Pro-Pro ↓ Gly-Pro, (SEQ ID NO: 33)
        Pro-Arg-Pro-Pro ↓ Thr-Pro, (SEQ ID NO: 34)
        Val-Val-Ala-Pro-Pro ↓ Ala-Pro, (SEQ ID NO: 35)
        Val-Val-Ala-Pro-Pro ↓ Ser-Pro (SEQ ID NO: 36)
        Val-Val-Ala-Pro-Pro ↓ Thr-Pro (SEQ ID NO: 37)
        Val-Val-Ala-Pro-Pro ↓ Gly-Pro (SEQ ID NO: 39)
        Ala-Pro-Pro-Ala ↓ Ala-Pro, (SEQ ID NO: 40)
        Pro-Arg-Pro-Pro ↓ Ala-Pro.

(SEQ ID NO: 41)
        Pro-Arg-Pro-Pro ↓ Ser-Pro (SEQ ID NO: 42)
        Pro-Arg-Pro-Pro ↓ Gly-Pro
```

The term "operably linked" denotes a juxtaposition of two or more components, wherein the components so described are in a relationship permitting them to function in their intended manner. For example, joining two polypeptide encoding regions such as a secretory leader and a polypeptide.

Linking of amino acid sequence encoding nucleic acid is accomplished by recombinant methods known in the art, e.g., using PCR methodology and/or by ligation at convenient restriction sites. If convenient restriction sites do not exist, then synthetic oligonucleotide adaptors or linkers are used in accord with conventional practice.

For the recombinant production of a polypeptide of interest in a prokaryotic cell among other things high expression yield and practicable down stream processing are envisaged.

A pro-polypeptide comprising in N- to C-terminal direction
 a first dipeptide GS,
 an amino acid sequence tag,
 a second dipeptide GS, and
 an enzymatic cleavage site
as reported herein is useful for the expression of an operably linked polypeptide of interest. The advantageous properties can be exerted when the pro-polypeptide as reported herein is fused to the N-terminus of a polypeptide of interest, which is intended to be expressed by recombinant means in a prokaryotic cell. Thus, the pro-polypeptide as reported herein can be used to improve expression yield and downstream processing. The polypeptide of interest is expressed by the prokaryotic cell as fusion polypeptide comprising the pro-polypeptide as reported herein and the polypeptide of interest. That is the fusion polypeptide comprises in N- to C-terminal direction the pro-polypeptides as reported herein and the polypeptide of interest.

TABLE 1

Expression yield of different fusion polypeptides. The first yield value given in each cell was obtained with a fermentation method according to Example 3b, the second yield value in each cell was obtained with a fermentation method according to Example 3a.

| elements of the N-terminal pro-polypeptide of the fusion polypeptide | | | | | | | | | |
|---|---|---|---|---|---|---|---|---|---|
| leading amino acid sequence | dipep-tide | amino acid sequence tag | dipep-tide | intervening amino acid sequence | enzymatic cleavage site | molecular weight of the fusion polypeptide | yield | yield [10$^{-3}$] | SEQ ID NO: |
| MR | GS | HHHHHH (SEQ ID NO: 11) | GS | n.p. | PRPPTP (SEQ ID NO: 33) | 34904.1 | 24.3 12.8 | 0.696 0.367 | 79 |
| MCDLP QTHSL (SEQ ID NO: 6) | GS | HHHHHH (SEQ ID NO: 11) | GS | n.p. | VVAPPAP. (SEQ ID NO: 34) | 35472.7 | 20.3 10.5 | 0.572 0.296 | 80 |
| MR | GS | HHHHHH (SEQ ID NO: 11) | GS | AEAGITGTWYNQL GSTFIVTAGADGA LTGTYESAVGNAE SRYVLTGRYDSAP | VVAPPAP. (SEQ ID NO: 34) | 48373.5 | 7.9 3.5 | 0.163 0.072 | 81 |

TABLE 1-continued

Expression yield of different fusion polypeptides. The first yield value given in each cell was obtained with a fermentation method according to Example 3b, the second yield value in each cell was obtained with a fermentation method according to Example 3a.

| | | elements of the N-terminal pro-polypeptide of the fusion polypeptide | | | | | | | |
|---|---|---|---|---|---|---|---|---|---|
| leading amino acid sequence | dipeptide | amino acid sequence tag | dipeptide | intervening amino acid sequence | enzymatic cleavage site | molecular weight of the fusion polypeptide | yield | yield [10$^{-3}$] | SEQ ID NO: |
| | | | | ATDGSGTALGWTV AWKNNYRNAHSAT TWSGQYVGGAEAR INTQWLLTSGTTE ANAWKSTLVGHDT FTKVKPSAAS_ (SEQ ID NO: 34) | | | | | |
| MR | GS | HHHHHH_ (SEQ ID NO: 11) | n.p. | AHFWQQA_ (SEQ ID NO: 2) | PRPPTP_ (SEQ ID NO: 38) | 35372.5 | 9.0 2.4 | 0.254 0.068 | 82 |
| MR | GS | HHHHHH_ (SEQ ID NO: 11) | n.p. | TDPEFQQQQQLLD VVKRQQELLRLTV WGTKNLQARVTAI EKYLQDQARLNSW GCAFRQVCHTTVP WVNDSLAPDWDNM TWQEWEKQVRYLE ANISKSLEQAQIQ QEKNMYELQKLNS WDIRSVV_ (SEQ ID NO: 8) | APPAAP_ (SEQ ID NO: 39) | 49653.5 | 10.2 7.0 | 0.205 0.141 | 85 |
| M | n.p. | HHHHHH_ (SEQ ID NO: 11) | n.p. | KAKRFKKH (SEQ ID NO: 1) | PRPPAP_ (SEQ ID NO: 40) | 35453.9 | 11.1 2.6 | 0.313 0.073 | 84 | n.p. = not present

From Table 1 it can be seen that fusion polypeptides comprising the pro-polypeptide as reported herein at the N-terminus in which between the second dipeptides GS and the enzymatic cleavage site no additional amino acid sequence is inserted provide for higher expression yield than those comprising an intervening amino acid sequence. A leading amino acid sequence of two or more amino acid residues may be present N-terminal to the first dipeptide GS.

At its C-terminus the pro-polypeptide as reported herein contains an enzymatic cleavage site. The enzymatic cleavage site is an amino acid sequence that contains a recognition motif for a protease. This recognition site can be for any protease as long as the protease cleaves specifically at this recognition site, i.e. this sequence occurs only once in the entire amino acid sequence of the fusion polypeptide.

Especially advantageous is the possibility for endotoxin removal while the fusion polypeptide is bound to an affinity chromatography material, i.e. to an affinity material that has not specifically been designed for the polypeptide of interest but for the amino acid sequence tag. With these binding properties any corresponding combination of amino acid sequence tag and corresponding affinity material can be used. After the endotoxin removal the polypeptide of interest can efficiently be recovered from the fusion polypeptide by using the protease cleavage site.

The following examples are provided to aid the understanding of the present invention, the true scope of which is set forth in the appended claims. It is understood that modifications can be made in the procedures set forth without departing from the spirit of the invention.

EXAMPLES

Materials & Methods

Recombinant DNA Techniques

Standard methods were used to manipulate DNA as described in Sambrook, J., et al., Molecular Cloning: A Laboratory Manual; Cold Spring Harbor Laboratory Press, 2nd edition, New York, (December 1989). The molecular biological reagents were used according to the manufacturer's instructions.

Gene Synthesis

Desired gene segments were prepared from oligonucleotides made by chemical synthesis. The gene segments, which are flanked by singular restriction endonuclease cleavage sites, were assembled by annealing and ligation of oligonucleotides including PCR amplification and subsequently cloned into the pCR2.1-TOPO-TA cloning vector (Invitrogen Corp., USA) via A-overhangs. The DNA sequence of the subcloned gene fragments were confirmed by DNA sequencing.

Example 1

Making and Description of the *E. coli* Expression Plasmids

The tetranectin-apolipoprotein A1 fusion polypeptide was prepared by recombinant means. The amino acid sequence of three different tetranectin-apolipoprotein A1 fusion polypeptides is given below (bold, tetranectin-trimerization domain, variant A and B). Variant A differs from variant B by the addition of two amino acid residues at the N-terminus of the tetranectin domain. Variant C differs from variant A by the addition of five amino acid residues at the C-terminal end of the tetranectin domain.

```
Amino acid sequence of Variant A (SEQ ID NO: 44):
  1  IVNAKKDVVN TKMFEELKSR LDTLAQEVAL LKEQQALQTV DEPPQSPWDR

51  VKDLATVYVD VLKDSGRDYV SQFEGSALGK QLNLKLLDNW DSVTSTFSKL

101  REQLGPVTQE FWDNLEKETE GLRQEMSKDL EEVKAKVQPY LDDFQKKWQE

151  EMELYRQKVE PLRAELQEGA RQKLHELQEK LSPLGEEMRD RARAHVDALR

201  THLAPYSDEL RQRLAARLEA LKENGGARLA EYHAKATEHL STLSEKAKPA

251  LEDLRQGLLP VLESFKVSFL SALEEYTKKL NTQ

Amino acid sequence of Variant B (SEQ ID NO: 77):
  1  KKIVNAKKD VVNTKMFEEL KSRLDTLAQE VALLKEQQAL QTVDEPPQSP

51  WDRVKDLATV YVDVLKDSGR DYVSQFEGSA LGKQLNLKLL DNWDSVTSTF

101  SKLREQLGPV TQEFWDNLEK ETEGLRQEMS KDLEEVKAKV QPYLDDFQKK

151  WQEEMELYRQ KVEPLRAELQ EGARQKLHEL QEKLSPLGEE MRDRARAHVD

201  ALRTHLAPYS DELRQRLAAR LEALKENGGA RLAEYHAKAT EHLSTLSEKA

251  KPALEDLRQG LLPVLESFKV SFLSALEEYT KKLNTQ

Amino acid sequence of Variant C (SEQ ID NO: 78):
  1  IVNAKKDVVN TKMFEELKSR LDTLAQEVAL LKEQQALQTV SLKGTDEPPQ

51  SPWDRVKDLA TVYVDVLKDS GRDYVSQFEG SALGKQLNLK LLDNWDSVTS

101  TFSKLREQLG PVTQEFWDNL EKETEGLRQE MSKDLEEVKA KVQPYLDDFQ

151  KKWQEEMELY RQKVEPLRAE LQEGARQKLH ELQEKLSPLG EEMRDRARAH

201  VDALRTHLAP YSDELRQRLA ARLEALKENG GARLAEYHAK ATEHLSTLSE

251  KAKPALEDLR QGLLPVLESF KVSFLSALEE YTKKLNTQ
```

The tetranectin-apolipoprotein A1 fusion polypeptides were expressed as precursor polypeptides (larger fusion polypeptides) in *E. coli*. The following N-terminal pro-polypeptides were tested for improved expression yield and downstream processing:

1) Amino acid sequence of pro-polypeptide combined with variant B (plasmid 5803):

```
                                         (SEQ ID NO: 79)
        MRGSHHHHHH GSPRPPTP
```

Pro-polypeptide 5803 is an artificial polypeptide comprising in N- to C-terminal direction:
  a leading amino acid sequence that has the amino acid sequence MR,
  a first dipeptide GS,
  a hexa-histidine tag that has the amino acid sequence of HHHHHH (SEQ ID NO: 11),
  a second dipeptide GS, and
  an IgA protease cleavage site that has the amino acid sequence of PRPPTP (SEQ ID NO: 33).

2) Amino acid sequence of pro-polypeptide combined with variant A (plasmid 5816):

```
                                         (SEQ ID NO: 80)
        MCDLPQTHSL GSHHHHHHGS VVAPPAP
```

Pro-polypeptide 5816 is an artificial polypeptide comprising in N- to C-terminal direction:
  a leading amino acid sequence encoding a methionine conjugated to a fragment of an interferon sequence with the amino acid sequence of MCDLPQTHSL (SEQ ID NO: 06),
  a first dipeptide GS,
  a hexa-histidine tag that has the amino acid sequence of HHHHHH (SEQ ID NO: 11),
  a second dipeptide GS, and
  an IgA protease cleavage site that has the amino acid sequence of VVAPPAP (SEQ ID NO: 34)

3) Amino acid sequence of pro-polypeptide combined with variant A (plasmid 5820):

```
                                                                         (SEQ ID NO: 81)
  1  MRGSHHHHHH GSAEAGITGT WYNQLGSTFI VTAGADGALT GTYESAVGNA

51  ESRYVLTGRY DSAPATDGSG TALGWTVAWK NNYRNAHSAT TWSGQYVGGA

101  EARINTQWLL TSGTTEANAW KSTLVGHDTF TKVKPSAASV VAPPAP
```

Pro-polypeptide 5820 is an artificial polypeptide comprising in N- to C-terminal direction:
- a leading amino acid sequence that has the amino acid sequence MR,
- a first dipeptide GS,
- a hexa-histidine tag that has the amino acid sequence of HHHHHH (SEQ ID NO: 11),
- a second dipeptide GS,
- an intervening amino acid sequence derived from streptavidin, and
- an IgA protease cleavage site that has the amino acid sequence of VVAPPAP (SEQ ID NO: 34)

4) Amino acid sequence of pro-polypeptide combined with variant A (plasmid 5805):

(SEQ ID NO: 82)
MRGSHHHHHH AHFWQQAPRP PTP

Pro-polypeptide 5805 is an artificial polypeptide comprising in N- to C-terminal direction:
- a leading amino acid sequence that has the amino acid sequence MR,
- a first dipeptide GS,
- a hexa-histidine tag that has the amino acid sequence of HHHHHH (SEQ ID NO: 11),
- an intervening amino acid sequence that has the amino acid sequence AHFWQQA (SEQ ID NO: 02), and
- an IgA protease cleavage site that has the amino acid sequence of PRPPTP (SEQ ID NO: 38)

5) Amino acid sequence of pro-polypeptide combined with variant C (plasmid 5819):

(SEQ ID NO: 83)
```
1   MRGSHHHHHH TDPEFQQQQQ LLDVVKRQQE LLRLTVWGTK NLQARVTAIE

51  KYLQDQARLN SWGCAFRQVC HTTVPWVNDS LAPDWDNMTW QEWEKQVRYL

101 EANISKSLEQ AQIQQEKNMY ELQKLNSWDI RSVVAPPAP
```

Pro-polypeptide 5819 is an artificial polypeptide comprising in N- to C-terminal direction:
- a leading amino acid sequence that has the amino acid sequence MR,
- a first dipeptide GS,
- a hexa-histidine tag that has the amino acid sequence of HHHHHH (SEQ ID NO: 11),
- an intervening amino acid sequence derived from the human HIV2 gp32 protein, and
- an IgA protease cleavage site that has the amino acid sequence of VVAPPAP (SEQ ID NO: 34)

6) Amino acid sequence of pro-polypeptide combined with variant B (plasmid 5806):

(SEQ ID NO: 84)
MHHHHHHKAK RFKKHPRPPAP

Pro-polypeptide 5806 is an artificial polypeptide comprising in N- to C-terminal direction:
- a leading amino acid sequence (M, start codon),
- a hexa-histidine tag that has the amino acid sequence of HHHHHH (SEQ ID NO: 11),
- an intervening amino acid sequence that has the amino acid sequence of KAKRFKKH (SEQ ID NO: 01), and
- an IgA protease cleavage site that has the amino acid sequence of PRPPAP (SEQ ID NO: 40)

The tetranectin-apolipoprotein A1 variant polypeptides were recovered from the fusion precursor protein by enzymatic cleavage in vitro using IgA protease.

The different pro-polypeptide tetranectin-apolipoprotein A1 encoding fusion genes, designated 5803, 5816, 5820, 5805, 5819 and 5806, were assembled with known recombinant methods and techniques by connection of appropriate nucleic acid segments. Nucleic acid sequences made by chemical synthesis were verified by DNA sequencing.

Making and Description of the Basic/Starting E. Coli Expression Plasmid 4980

Plasmid 4980 (4980-pBRori-URA3-LACI-SAC) is an expression plasmid for the expression of core-streptavidin in E. coli. It was generated by ligation of the 3142 bp long EcoRI/CelII-fragment derived from plasmid 1966 (1966-pBRori-URA3-LACI-T-repeat; reported in EP-B 1 422 237) with the 435 bp long core-streptavidin encoding EcoRI/CelII-fragment.

The core-streptavidin E. coli expression plasmid comprises the following elements:
- the origin of replication from the vector pBR322 for replication in E. coli (corresponding to by position 2517-3160 according to Sutcliffe, J. G., et al., Quant. Biol. 43 (1979) 77-90),
- the URA3 gene of Saccharomyces cerevisiae coding for orotidine 5'-phosphate decarboxylase (Rose, M., et al., Gene 29 (1984) 113-124) which allows plasmid selection by complementation of E. coli pyrF mutant strains (uracil auxotrophy),
- the core-streptavidin expression cassette built up of
  - the T5 hybrid promoter (T5-PN25/03/04 hybrid promoter according to Bujard, H., et al., Methods. Enzymol. 155 (1987) 416-433 and Stueber, D., et al., Immunol. Methods IV (1990) 121-152) including a synthetic ribosomal binding site according to Stüber, D., et al., (see before),
  - the core-streptavidin gene, and
  - two bacteriophage-derived transcription terminators, the λ-T0 terminator (Schwarz, E., et al., Nature 272 (1978) 410-414) and the fd-terminator (Beck, E., and Zink, B., Gene 1-3 (1981) 35-58), and
- the lacI repressor gene from E. coli (Farabaugh, P. J., Nature 274 (1978) 765-769).

Making of the Final Expression Plasmids Comprising Pro-Polypeptides (Plasmids 5803, 5816, 5820, 5805, 5819 and 5806)

Plasmid 5803 (5803-His6-IgA-TP7-TripB-ApoAI) ("His6" disclosed as SEQ ID NO: 11) is the plasmid for the expression of the tetranectin-apolipoprotein A1 precursor protein containing pro-polypeptide 5803. It was prepared by excising the core-streptavidin structural gene from vector 4980 using the singular flanking EcoRI and CelII restriction endonuclease cleavage site and insertion of the 958 bp long EcoRII/CelII 5803 pro-polypeptide tetranectin-apolipoprotein A1 precursor protein encoding gene segment into the 3142 bp long EcoRI/CelII-4980 vector fragment.

Plasmids ("his6" Disclosed as SEQ ID NO: 11 in the Following):
5816 (5816-IFN-His6-IgA-API10-TripB-ApoAI),
5820 (5820-His6-coreSA-IgA-API10-TripB-ApoA1),
5805 (5805-His6-IgA-Pro-TPI10-TripB-ApoAI),
5819 (5819-gp32-His6-IgA-API10-TriB-SLKGT-ApoA1), and
5806 (5806-His6-IgA-Opt-AP7-TripB-ApoAI)
were generated as described before for plasmid 5803.

Example 2

Expression of the Tetranectin-Apolipoprotein A1 Precursor Protein from Plasmids 5803, 5816, 5820, 5805, 5819 and 5806 in E. coli For the expression of the tetranectin-apolipoprotein A1 precursor proteins 5803, 5816, 5820, 5805, 5819 and 5806 an E. coli host/vector system was employed which enables an antibiotic-free plasmid selection by complementation of an E. coli auxotrophy (PyrF) (see e.g. EP-B 0 972 838 and U.S. Pat. No. 6,291,245).

The tetranectin-apolipoprotein A1 precursor proteins were expressed in the E. coli strain CSPZ-2 (leuB, proC, trpE, thi-1, ΔpyrF).

Transformation and Cell Culturing by Complementation of a pyrF Auxotrophy in Selective Medium The E. coli K12 strain CSPZ-2 (leuB, proC, trpE, thi-1, ΔpyrF) was transformed with the expression plasmids (5803, 5816, 5820, 5805, 5819 and 5806, respectively) obtained in previous step. The transformed CSPZ-2 cells were first grown at 37° C. on agar plates and subsequently in a shaking culture in M9 minimal medium containing 0.5% casamino acids (Difco) up to an optical density at 550 nm (OD550) of 0.6-0.9 and subsequently induced with IPTG (1-5 mmol/l final concentration).

After an induction phase of 4 to 16 hours at 37° C. the cytoplasmic and soluble expressed tetranectin-apolipoprotein A1 precursor proteins were transferred to insoluble protein aggregates, the so called inclusion bodies, with a heat step where the whole culture broths in the Erlenmeyer flasks were heated to 50° C. for 1 or 2 hours before harvest (see e.g. EP-B 1 486 571). Thereafter, the cells were harvested by centrifugation, washed with 50 mmol/l potassium phosphate buffer, pH 6.5, and stored at −20° C. until further processing.

Expression Analysis

For expression analysis cell pellets from 3 OD550 nm units (1 OD550 nm=1 ml cell suspension with an OD at 550 nm of 1) of centrifuged culture medium were resuspended in 0.25 ml 10 mmol/l potassium phosphate buffer, pH 6.5, and the cells were lysed by ultrasonic treatment (two pulses of 30 sec. at 50% intensity). The insoluble cell components were sedimented (centrifugation 14,000 rpm, 5 min.) and the supernatant was admixed with ⅕ of its volume 5×SDS sample buffer (1×SDS sample buffer: 50 mmol/l Tris-HCl, pH 6.8, 1% SDS, 50 mmol/l DTT, 10% glycerol, 0.001% bromophenol blue). The insoluble cell debris fraction (pellet) was resuspended in 0.3 ml 1×SDS sample buffer, the samples were incubated for 5 min. at 95° C. and centrifuged again. Subsequently, the proteins were separated by SDS polyacrylamide gel electrophoresis (PAGE) (Laemmli, U.K., Nature 227 (1970) 680-685) and stained with Coomassie Brilliant Blue R dye.

The synthesized tetranectin-apolipoprotein A1 precursor proteins were homogeneous and found in the insoluble cell debris fraction in the form of insoluble protein aggregates (IBs). The expression yield was comparable within the scope of the measurement accuracy in all clones and was between 30-60% relative to the total E. coli protein.

Example 3

10 l High Cell Density Fermentations of E. coli for the Recombinant Production of the Tetranectin-Apolipoprotein A1 Precursor Proteins Example 3a Pre-Culture For pre-fermentation a M9 medium according to Sambrook, J., et al., (Molecular Cloning: A Laboratory Manual; Cold Spring Harbor Laboratory Press; 2nd edition, New York, (December 1989)) supplemented with about 1 g/l L-leucine, about 1 g/l L-proline and about 1 mg/l thiamine-HCl has been used.

For pre-fermentation 300 ml of M9-medium in a 1000 ml Erlenmeyer-flask with baffles was inoculated with 2 ml out of a primary seed bank ampoule. The cultivation was performed on a rotary shaker for 13 hours at 37° C. until an optical density (578 nm) of 1-3 was obtained.

10 l Fed-Batch Main Fermentation

For fermentation a batch medium according to Riesenberg, et al., was used (Riesenberg, D., et al., J. Biotechnol. 20 (1991) 17-27): 27.6 g/l glucose*$H_2O$, 13.3 g/l $KH_2PO_4$, 4.0 g/l $(NH_4)_2HPO_4$, 1.7 g/l citrate, 1.2 g/l $MgSO_4$*7 $H_2O$, 60 mg/l iron(III)citrate, 2.5 mg/l $CoCl_2$*6 $H_2O$, 15 mg/l $MnCl_2$*4 $H_2O$, 1.5 mg/l $CuCl_2$*2 $H_2O$, 3 mg/l $H_3BO_3$, 2.5 mg/l $Na_2MoO_4$*2 $H_2O$, 8 mg/l $Zn(CH_3COO)_2$*2 $H_2O$, 8.4 mg/l TITRIPLEX III™, 1.3 ml/l SYNPERONIC™ 10% anti foam agent. The batch medium was supplemented with 5.4 mg/l Thiamin-HCl and 1.2 g/l L-leucine and L-proline respectively. The feed 1 solution contained 700 g/l glucose supplemented with 19.7 g/l $MgSO_4$*7 $H_2O$. The alkaline solution for pH regulation was an aqueous 12.5% (w/v) $NH_3$ solution supplemented with 50 g/l L-leucine and 50 g/l L-proline respectively. All components were dissolved in deionized water.

The fermentation was carried out in a 10 l BIOSTAT™ C DCU3 fermenter (Sartorius, Melsungen, Germany). Starting with 6.4 l sterile fermentation batch medium plus 300 ml inoculum from the pre-fermentation the batch fermentation was performed at 37° C., pH 6.9±0.2, 500 mbar and an aeration rate of 10 l/min. After the initially supplemented glucose was depleted the temperature was shifted to 28° C. and the fermentation entered the fed-batch mode. Here the relative value of dissolved oxygen (pO2) was kept at 50% (DO-stat, see e.g. Shay, L. K., et al., J. Indus. Microbiol. (1987) 79-85) by adding feed 1 in combination with constantly increasing stirrer speed (550 rpm to 1000 rpm within 10 hours and from 1000 rpm to 1400 rpm within 16 hours) and aeration rate (from 10 l/min to 16 l/min in 10 hours and from 16 l/min to 20 l/min in 5 hours). The supply with additional amino acids resulted from the addition of the alkaline solution, when the pH reached the lower regulation limit (6.70) after approximately 8 hours of cultivation. The expression of recombinant therapeutic protein was induced by the addition of 1 mM IPTG at an optical density of 70.

Harvesting the Biomass

At the end of fermentation the cytoplasmatic and soluble expressed tetranectin-apolipoprotein A1 is transferred to insoluble protein aggregates, the so called inclusion bodies, with a heat step where the whole culture broth in the fermenter is heated to 50° C. for 1 or 2 hours before harvest (see e.g. EP-B 1 486 571). Thereafter, the content of the fermenter was centrifuged with a flow-through centrifuge (13,000 rpm, 13 l/h) and the harvested biomass was stored at −20° C. until further processing. The synthesized tetranectin-apolipoprotein A1 precursor proteins were found exclusively in the insoluble cell debris fraction in the form of insoluble protein aggregates, so-called inclusion bodies (IBs).

Product Quantification

Samples drawn from the fermenter, one prior to induction and the others at dedicated time points after induction of protein expression are analyzed with SDS-Polyacrylamide gel electrophoresis. From every sample the same amount of cells ($OD_{Target}=5$) are resuspended in 5 mL PBS buffer and disrupted via sonication on ice. Then 100 μL of each suspension are centrifuged (15,000 rpm, 5 minutes) and each supernatant is withdrawn and transferred to a separate vial. This is to discriminate between soluble and insoluble expressed target protein. To each supernatant (=soluble) fraction 300 μL and to each pellet (=insoluble) fraction 400 μL of SDS sample buffer (Laemmli, U.K., Nature 227 (1970) 680-685) are added. Samples are heated for 15 minutes at 95° C. under shaking to solubilize and reduce all proteins in the samples. After cooling to room temperature 5 μL of each sample are transferred to a 4-20% TGX CRITERION™ Stain Free polyacrylamide gel (Bio-Rad). Additionally 5 μl molecular weight standard (PRECISION PLUS™ Protein Standard, Bio-Rad) and 3 amounts (0.3 μl, 0.6 μl and 0.9 μl) quantification standard with known product protein concentration (0.1 μg/μl) are positioned on the gel.

The electrophoresis was run for 60 Minutes at 200 V and thereafter the gel was transferred the GELDOC EZ™ Imager (Bio-Rad) and processed for 5 minutes with UV radiation. Gel images were analyzed using IMAGE LAB™ analysis software (Bio-Rad). With the three standards a linear regression curve was calculated with a coefficient of >0.99 and thereof the concentrations of target protein in the original sample was calculated.

Example 3b

Pre-Culture

For pre-fermentation a M9 medium according to Sambrook et al. (Molecular Cloning: A laboratory manual. Cold Spring Harbor Laboratory Press; 2nd edition (December 1989)) supplemented with about 1 g/l L-leucine, about 1 g/l L-proline and about 1 mg/l thiamine-HCl has been used.

For pre-fermentation 300 ml of modified M9-medium in a 1000 ml Erlenmeyer-flask with baffles was inoculated from agar plate or with 1-2 ml out of a primary seed bank ampoule. The cultivation was performed on a rotary shaker for 13 hours at 37° C. until an optical density (578 nm) of 1-3 was obtained.

10 l Fed-Batch Main Fermentation

For fermentation and high yield expression of tetranectin-apolipoprotein A1 the following batch medium and feeds were used (Schantz, previously unpublished):

8.85 g/l glucose, 63.5 g/l yeast extract, 2.2 g/l $NH_4Cl$, 1.94 g/l L-leucine, 2.91 g/l L-proline, 0.74 g/l L-methionine, 17.3 g/l $KH_2PO_4*H2_O$, 2.02 g/l $MgSO_4*7\ H_2O$, 25.8 mg/l Thiamin-HCl, 1.0 ml/l SYNPERONIC™ 10% anti foam agent. The feed 1 solution contained 333 g/l yeast extract and 333 g/l 85%-glycerol supplemented with 1.67 g/l L-methionine and 5 g/l L-leucine and L-proline each. The feed 2 was a solution of 600 g/l L-Proline. The alkaline solution for pH regulation was a 10% (w/v) KOH solution and as acid a 75% glucose solution was used. All components were dissolved in deionized water.

The fermentation was carried out in a 10 l BIOSTAT™ C DCU3 fermenter (Sartorius, Melsungen, Germany). Starting with 5.15 l sterile fermentation batch medium plus 300 ml inoculum from the pre-fermentation the fed-batch fermentation was performed at 25° C., pH 6.7±0.2, 300 mbar and an aeration rate of 10 l/min. Before the initially supplemented glucose was depleted the culture reached an optical density of 15 (578 nm) and the fermentation entered the fed-batch mode when feed 1 was started with 70 g/h. Monitoring the glucose concentration in the culture the feed 1 was increased to a maximum of 150 g/h while avoiding glucose accumulation and keeping the pH near the upper regulation limit of 6.9. At an optical density of 50 (578 nm) feed 2 was started with a constant feed rate of 10 ml/h. The relative value of dissolved oxygen ($pO_2$) was kept above 50% by increasing stirrer speed (500 rpm to 1500 rpm), aeration rate (from 10 l/min to 20 l/min) and pressure (from 300 mbar to 500 mbar) in parallel. The expression of recombinant therapeutic protein was induced by the addition of 1 mM IPTG at an optical density of 90.

Product Quantification

Seven samples drawn from the fermenter, one prior to induction and the others at dedicated time points after induction of protein expression are analyzed with SDS-Polyacrylamide gel electrophoresis. From every sample the same amount of cells ($OD_{Target}=5$) are resuspended in 5 mL PBS buffer and disrupted via sonication on ice. Then 100 μL of each suspension are centrifuged (15,000 rpm, 5 minutes) and each supernatant is withdrawn and transferred to a separate vial. This is to discriminate between soluble and insoluble expressed target protein. To each supernatant (=soluble) fraction 300 μL and to each pellet (=insoluble) fraction 200 μL of SDS sample buffer (Laemmli, U.K., Nature 227 (1970) 680-685) are added. Samples are heated for 15 minutes at 95° C. under shaking to solubilize and reduce all proteins in the samples. After cooling to room temperature 5 μL of each sample are transferred to a 10% Bis-Tris polyacrylamide gel (Novagen). Additionally 5 μl molecular weight standard (PRECISION PLUS™ Protein Standard, Bio-Rad) and 3 amounts (0.3 μl, 0.6 μl and 0.9 μl) quantification standard with known product protein concentration (0.1 μg/μl) are positioned on the gel.

The electrophoresis was run for 35 minutes at 200 V and then the gel was stained with Coomassie Brilliant Blue R dye, destained with heated water and transferred to an optical densitometer for digitalization (GS710, Bio-Rad). Gel images were analyzed using QUANTITY ONE™ 1-D analysis software (Bio-Rad). With the three standards a linear regression curve is calculated with a coefficient of >0.98 and thereof the concentrations of target protein in the original sample was calculated.

Harvesting the Biomass

At the end of fermentation the cytoplasmatic and soluble expressed tetranectin-apolipoprotein A1 is transferred to insoluble protein aggregates, the so called inclusion bodies (IBs), with a heat step where the whole culture broth in the fermenter is heated to 50° C. for 1 or 2 hours before harvest (see e.g. EP-B 1 486 571). After the heat step the synthesized tetranectin-apolipoprotein A1 precursor proteins were found exclusively in the insoluble cell debris fraction in the form of IBs.

The contents of the fermenter are cooled to 4-8° C., centrifuged with a flow-through centrifuge (13,000 rpm, 13 l/h) and the harvested biomass is stored at −20° C. until further processing. The total harvested biomass yield ranged between 39 g/l and 90 g/l dry matter depending on the expressed construct.

The invention claimed is:

1. A fusion polypeptide comprising in N- to C-terminal direction:
- a leading amino acid sequence of SEQ ID NO. 06;
- a first dipeptide GS;
- an amino acid sequence tag having the amino acid sequence of SEQ ID NO. 11;
- a second dipeptide GS adjacent thereto;
- an enzymatic cleavage site having the amino acid sequence of SEQ ID NO. 34; and
- a polypeptide of interest having the amino acid sequence of SEQ ID NO. 43, SEQ ID NO. 44 or SEQ ID NO. 45.

2. The fusion polypeptide according to claim 1, wherein the amino acid at the N-terminus of the fusion polypeptide has a free alpha-amino group.

3. The fusion polypeptide of claim 1, wherein said polypeptide of interest has the amino acid sequence of SEQ ID NO. 43.

4. The fusion polypeptide of claim 1, wherein said polypeptide of interest has the amino acid sequence of SEQ ID NO. 44.

5. The fusion polypeptide of claim 1, wherein said polypeptide of interest has the amino acid sequence of SEQ ID NO. 45.

6. A fusion polypeptide comprising in N- to C-terminal direction:
- a pro-peptide having the amino acid sequence of SEQ ID NO. 80; and
- a polypeptide of interest having the amino acid sequence of SEQ ID NO. 43, SEQ ID NO. 44 or SEQ ID NO. 45.

7. The fusion polypeptide of claim 6, wherein said polypeptide of interest has the amino acid sequence of SEQ ID NO. 43.

8. The fusion polypeptide of claim 6, wherein said polypeptide of interest has the amino acid sequence of SEQ ID NO. 44.

9. The fusion polypeptide of claim 6, wherein said polypeptide of interest has the amino acid sequence of SEQ ID NO. 45.

* * * * *